(12) United States Patent
Bishop et al.

(10) Patent No.: US 12,351,597 B2
(45) Date of Patent: Jul. 8, 2025

(54) SUBSTITUTED BIPHENYL OR PHENYLHETEROARYL-MANNOSIDES AS ANTAGONISTS OF FIMH

(71) Applicants: GLAXOSMITHKLINE INTELLECTUAL PROPERTY DEVELOPMENT LIMITED, Middlesex (GB); FIMBRION THERAPEUTICS, INC., Saint Louis, MO (US)

(72) Inventors: Michael Joseph Bishop, Collegeville, PA (US); James Walter Janetka, Saint Louis, MO (US); Laurel Kathryn McGrane, Saint Louis, MO (US); Katherine Louisa Widdowson, Collegeville, PA (US)

(73) Assignees: GlaxoSmithKline Intellectual Property Development Limited, Stevenage (GB); Fimbrion Therapeutics, Inc, Saint Louis, MO (US)

( * ) Notice: Subject to any disclaimer, the term of this patent is extended or adjusted under 35 U.S.C. 154(b) by 774 days.

(21) Appl. No.: 17/617,642

(22) PCT Filed: Jun. 17, 2020

(86) PCT No.: PCT/EP2020/066707
§ 371 (c)(1),
(2) Date: Dec. 9, 2021

(87) PCT Pub. No.: WO2020/254369
PCT Pub. Date: Dec. 24, 2020

(65) Prior Publication Data
US 2022/0242900 A1 Aug. 4, 2022

Related U.S. Application Data

(60) Provisional application No. 62/863,479, filed on Jun. 19, 2019.

(51) Int. Cl.
*C07H 15/26* (2006.01)
*C07H 15/23* (2006.01)

(52) U.S. Cl.
CPC .............. *C07H 15/26* (2013.01); *C07H 15/23* (2013.01)

(58) Field of Classification Search
None
See application file for complete search history.

(56) References Cited

U.S. PATENT DOCUMENTS

| | | |
|---|---|---|
| 6,153,396 A | 11/2000 | Hultgren |
| 6,962,791 B2 | 11/2005 | Hultgren |
| 7,790,183 B2 | 9/2010 | Darouiche |
| 8,937,167 B2 | 1/2015 | Janetka |
| 9,567,362 B2 | 2/2017 | Janetka |
| 9,957,289 B2 | 5/2018 | Janetka |
| 10,273,260 B2 | 4/2019 | Janetka |
| 10,738,070 B2 | 8/2020 | Janetka et al. |
| 2007/0167378 A1 | 7/2007 | Saraiva |
| 2008/0171706 A1 | 7/2008 | Berglund |
| 2008/0268006 A1 | 10/2008 | Molin |
| 2010/0015600 A1 | 1/2010 | Barnich |
| 2012/0309701 A1 | 12/2012 | Janetka |
| 2014/0243283 A1 | 8/2014 | Ramtohul et al. |
| 2014/0274930 A1 | 9/2014 | Dietrich |
| 2015/0175644 A1 | 6/2015 | Ernst |
| 2015/0197538 A1 | 7/2015 | Janetka |
| 2016/0145289 A1 | 5/2016 | Janetka |
| 2017/0247401 A1 | 8/2017 | Janetka |
| 2018/0194792 A1 | 7/2018 | Janetka |
| 2019/0106451 A1 | 4/2019 | Janetka |
| 2019/0211045 A1 | 7/2019 | Janetka |
| 2020/0002303 A1 | 1/2020 | Janetka |

FOREIGN PATENT DOCUMENTS

| | | |
|---|---|---|
| EP | 383092 | 1/1990 |
| WO | WO/1995/014028 | 5/1995 |
| WO | WO/2001/10386 | 2/2001 |
| WO | WO/2005/089733 | 9/2005 |
| WO | WO 2011/050323 A1 | 4/2011 |
| WO | WO/2011/073112 | 6/2011 |
| WO | WO/2012/109263 | 8/2012 |
| WO | WO/2012/164074 | 12/2012 |
| WO | WO 2013/134415 | 9/2013 |
| WO | WO 2014/016361 | 1/2014 |
| WO | WO 2014/055474 | 4/2014 |
| WO | WO 2014/100158 | 6/2014 |

(Continued)

OTHER PUBLICATIONS

Cusumano et al. "Treatment and Prevention of Urinary Tract Infection with Orally Active FimH Inhibitors", Science Translational Medicine, American Association for the Advancement of Science, 3(107-111): ra109-ra115 (Jan. 1, 2011).
Schönemann et al. "Improvement of Aglycone π-Stacking Yields Nanomolar to Sub-nanomolar FimH Antagonists", Chemmedchem, 14(7): 749-757 (Feb. 22, 2019).
Han et al. "Structure-Based Drug Design and Optimization of Mannoside Bacterial FimH Antagonists", Journal of Medicinal Chemistry, American Chemical Society, US, 53(12): 4779-4792 (2010).
Abdel-Megeid, F. et al., "Preparation and Some Reactions of O-Glucosyl Derivatives of 2-Thioxo-1,3,4-Oxadiazoles and 2-Thioxo-1,3,4-Thiadiazoles and Their 2-Oxo Analogues", Carbohydrate Res., 59(1):95-102, (1977).

(Continued)

*Primary Examiner* — Traviss C McIntosh, III
(74) *Attorney, Agent, or Firm* — Nora L. Stein

(57) ABSTRACT

Disclosed herein are new O-biphenyl- and O-phenylheteroarylmannoside compounds and compositions and their application as pharmaceuticals for use in the treatment of human disease. Methods of inhibition of FimH activity in human subjects are also provided for the treatment of diseases such as urinary tract infection.

7 Claims, No Drawings

(56) References Cited

FOREIGN PATENT DOCUMENTS

| WO | WO 2014/165107 | 10/2014 | | |
|---|---|---|---|---|
| WO | WO 2014/194270 A1 | 12/2014 | | |
| WO | WO/2017/021549 | 2/2017 | | |
| WO | WO/2017/156508 | 9/2017 | | |
| WO | WO-2017165619 A1 | * | 9/2017 | ......... A61K 31/7052 |
| WO | WO/2019/076931 | 4/2019 | | |

OTHER PUBLICATIONS

Abgottspon, D. et al., "Development of an Aggregation Assay to Screen FimH Antagonists", J Microb Methods, 82(3):249-55, (2010).

Abgottspon, D. et al., "In Vivo Evaluation of FimH Antagonists—A Novel Class of Antimicrobials for the Treatment of Urinary Tract Infection", Chimia, 66(4):166-9, (2012).

Almant M, Moreau V, Kovensky J, et al. "Clustering of Escherichia coli type-1 fimbrial adhesins by using multimeric heptyl a-D-mannoside probes with a carbohydrate core," Chem Eur J,17:10029-10038 (2011).

Aronson M, Medalia O, Schori L, et al. "Prevention of colonization of the urinary tract of mice with Escherichia coli by blocking of bacterial adherence with methyl alpha-D-mannopyranoside," J Infect Dis, 139:329-332 (1979).

Barras A, Martin FA, Bande O, et al. "Glycan-functionalized diamond nanoparticles as potent E. coli anti-adhesives," Nanoscale,5:2307-2316 (2013).

Bognar, R. et al., "N-Glycosyl Derivatives: Part III. The Subsequent Installation of the Aglycone. Synthesis of N-Glycosyl Derivatives of 2-Amino-Thiazole, 2-Amino-1 ,3,4-Thiadiazole and 5-Amino-1 ,2,3,4-Thiatriazols", Carbohy Res., 5:320-328, (1967).

Bouckaert, J. et al., "Receptor Binding Studies Disclose a Novel Class of High-Affinity Inhibitors of the Escherichia coli FimH Adhesion", Mol Microbiol., 55(2):441-55, (2005).

Bouckaert J, Li Z, Xavier C, et al. "Heptyl alpha-D-mannosides grafted on a beta-cyclodextrin core to interfere with Escherichia coli adhesion: an in vivo multivalent effect," Chemistry,19:7847-7855 (2013).

Car Z, Hrenar T, Petrović Peroković VP, et al. "Mannosylated N-aryl substituted 3-hydroxypyridine-4-ones: synthesis, hemagglutination inhibitory properties, and molecular modeling," Chem Biol Drug Des, 84:393-401 (2014).

Chandrasekaran V, Kolbe K, Beiroth F, et al. "Synthesis and testing of the first azobenzene mannobioside as photoswitchable ligand for the bacterial lectin FimH," Beilstein J Org Chem, 9:223-233 (2013).

Choudhury D, Thompson A, Stojanoff V, et al. "X-ray structure of the FimC-FimH chaperone-adhesin complex from uropathogenic Escherichia coli," Science,285:1061-1066 (1999).

De Ruyck J, Lensink MF, Bouckaert J, "Structures of C-mannosylated anti-adhesives bound to the type 1 fimbrial FimH adhesin," IUCrJ,3(Pt 3:163-167 (2016).

Durka, M. et al., "The Functional Valency of Dodecamannosylated Fullerenes with Escherichia coli FimH—Towards Novel Oacterial Antiadhesives", Chem Commun., 47(4):1321-3, (2011).

Firon, N. et al., "Aromatic Alpha-Glycosides of Mannose Are Powerful Inhibitors of the Adherence of Type 1 Fimbriated Escherichia coli to Yeast and Intestinal Epithelial Cells", Infect Immun., 55(2):472-6, (1987).

Firon, N et al., "Interaction of Mannose-Containing Oligosaccharides With the Fimbrial Lectin of Escherichia coli", Biochem and Biophys Res Commun., 105(4):1426-32, (1982).

Furneaux, R. et al., "New Mannotriosides and Trimannosides as Potential Ligands for Mannose-Specific Binding Oroteins", Can J Chem., 80:964-72, (2002).

Gouin, S. et al., "Synthetic Multimeric Heptyl Mannosides as Potent Antiadhesives of Uropathogenic Escherichia coli", Chem Med Chem., 4(5):749-55, (2009).

Grabosch, C. et al., "Squaric Acid Monoamide Mannosides as Ligands for the Bacterial Lectin FimH: Covalent nhibition or Not?", Chem Bio Chem., 12(7):1066-74, (2011).

Guiton, P. et al., "Combinatorial Small-Molecule Therapy Prevents Uropathogenic Escherichia coli Catheter-Associated Urinary Tract Infections in Mice", Antimicrob Agents Chemother., 56(9):4738-45, (2012).

Han, Z. et al., "Lead Optimization Studies on FimH Antagonists: Discovery of Potent and Orally Bioavailable Ortho-Substituted Biphenyl Mannosides", J Med Chem., 55(8):3945-59, (2012).

Hartmann, M. et al., "The Bacterial Lectin FimH, a Target for Drug Discovery—Carbohydrate Inhibitors of Type 1 Fimbriae-Mediated Bacterial Adhesion", Eur J Org Chem., 2011(20-21):3583-3609 (2011).

Haskins, W. et al., "Relations Between Rotatory Power and Structure in the Sugar Group; Some 2'-Naphthyl L-Thioglycopyranosides and their Acetates", J Am Chem Soc., 69(7):1668-72, (1947).

Hung, C. et al., "Structural Basis of Tropism of Escherichia coli to the Bladder During Urinary Tract Infection", Mol Microb., 44(4):903-15, (2002).

Irani, R. et al., "Stannic Chloride Promoted Synthesis of Mannosides", Indian J Chem., Sect. B: Org. Chem. Incl. Med. Chem. 30(5):519-21, (1991), (abstract only).

Jarvis C, Han Z, Kalas V, et al., "Antivirulence isoquinolone mannosides: optimization of the biaryl aglycone for FimH lectin binding affinity and efficacy in the treatment of chronic UTI," ChemMedChem,11(4):367-373 (2016).

Jiang, X. et al., "Antiadhesion Therapy for Urinary Tract Infections—A Balanced PK/PD Profile Proved To Be Key for Success", J Med Chem., 55(10):4700-13, (2012).

Kleeb S, Jiang X, Frei P, et al, "FimH antagonists: phosphate prodrugs improve oral bioavailability," J Med Chem, 59(7):3163-3182 (2016).

Kleeb S, Pang L, Mayer K, et al, "FimH antagonists: bioisosteres to improve the in vitro and in vivo PK/PD profile," J Med Chem, 58(5):2221-2239 (2015).

Klein, T. et al., "FimH Antagonists for the Oral Treatment of Urinary Tract Infections: From Design and Synthesis to in Vitro and in Vivo Evaluation", J Med Chem., 53(24):8627-41, (2010).

Kostakioti, M. et al., "Distinguishing the Contribution of Type 1 Pili from That of other QseB—Misregulated Factors When QseC Is Absent during Urinary Tract Infection", Infect Immun., 80(8):2826-34, (2012).

Kötter S, Krallmann-Wenzel U, Ehlers S, et al, "Multivalent ligands for the mannose-specific lectin on type 1 fimbriae of Escherichia coli: syntheses and testing of trivalent a-D-mannoside clusters," J Chem Soc Perkin Trans I,14:2193-2200 (1998).

Laurel Mydock-McGrane, et al. "Antivirulence C-Mannosides as Antibiotic-Sparing, Oral Therapeutics for Urinary Tract Infections". Journal of Medicinal Chemistry, vol. 59, No. 20, 9390-9408 (Oct. 14, 2016).

Lindhorst, T. et al., "Inhibition of the Type 1 Fimbriae-Mediated Adhesion of Escherichia coli to Erythrocytes by Multiantennary [alpha]-mannosyl Clusters: The Effect of Multivalency", Glycoconj J., 15(6):605-13, (1998).

Lindhorst TK, Bruegge K, Fuchs A, et al., "A bivalent glycopeptide to target two putative carbohydrate binding sites on FimH," Beilstein J Org Chem,6:801-809 (2010).

Nagahori, N. et al., "Inhibition of Adhesion of Type 1 Fimbriated Escherichia coli to Highly Mannosylated Ligands", ChemBioChem, 3(9):836-44, (2002).

Neeser, J, Koellreutter B, Wuersch P, "Oligomannoside-type glycopeptides inhibiting adhesion of Escherichia coli strains mediated by type 1 pili: preparation of potent inhibitors from plant glycoproteins," Infect Immun,52(4):428-436 (1986).

Pang, et al., "FimH Antagonists: Structure-Activity and Structure-Property Relationships for Biphenyl a-D-Mannopyranosides," ChemMedChem 2012, vol. 7, pp. 1404-1422, p. 1408.

Papadopoulos A, Shiao TC, Roy R, "Diazo transfer and click chemistry in the solid phase syntheses of lysine-based glycodendrimers as antagonists against Escherichia coli FimH," Mol Pharm,9:394-403 (2012).

Qian, X. et al., "Arrays of Self-Assembled Monolayers for Studying Inhibition of Bacterial Adhesion", Anal Chem., 74(8):1805-10, (2002).

(56) References Cited

OTHER PUBLICATIONS

Rabbani, S. et al., "Expression of the Carbohydrate Recognition Domain of FimH and Development of a Competitive Binding Assay", Anal Biochem., 407(2):188-95, (2010).
Sattigeri, J. et al., "Synthesis and Evaluation of Thiomannosides, Potent and Orally Active FimH Inhibitors", Bioorg Med Chem Lett., 28(17):2993-2997, (2018).
Scharenberg, M. et al., "Target Selectivity ofFimH Antagonists", J Med Chem., 55(22):9810-6, (2012).
Scharenberg, M. et al., "A Flow Cytometry-Based Assay for Screening FimH Antagonists", Assay Drug DevTechnol., 9(5):455-65, (2011).
Schierholt A, Hartmann M, Lindhorst TK, "Bi- and trivalent glycopeptide mannopyranosides as inhibitors of type 1 fimbriae-mediated bacterial adhesion: variation of valency, aglycon and scaffolding," Carb Res,346:1519-1526 (2011).
Schönemann W, Kleeb S, Dätwyler P, et al, Prodruggability of carbohydrates—oral FimH antagonists, Can J Chem,94 (11):909-919 (2016).
Schwardt, 0. et al., "Design, Synthesis and Biological Evaluation of Mannosyl Triazoles as FimH Antagonists", Bioorg Med Chem., 19(21):6454-73, (2011).
Shuman, D. et al., "Synthesis and Biological Activity of Certain 8-Mercaptopurine and 6-Mercaptopyrimidine S-Nucleosides", J Med Chem., 12(4):653-7, (1969).
Sperling, O. et al., "Evaluation of the Carbohydrate Recognition Domain of the Bacterial Adhesion FimH: Design, Synthesis and Binding Properties of Mannoside Ligands", Org Biomol Chem., 4(21):3913-3922, (2006).
Stoll, Van A. et al., "The Furocoumarin and the Beta-D-Glucosido-Furocumarinsaure from the Seeds of *Coronilla* Species", Helvetica Chimica Acta, 33(211-212):1637-47, (1950), (with English abstract).
Taile, V. et al., "Synthesis and Biological Evaluation of Novel 2(4-O-beta-D glucosidoxyphenyl) 4,5-Disubstituted Imidazoles", J Heterocyclic Chem., 47(4):903-7, (2010).
Tomašić T, Rabbani S, Gobec M, et al, "Branched: a-D-mannopyranosides: a new class of potent FimH antagonists," Med Chem Commun,5(8):1247-1253 (2014).
Touaibia, M. et al., "Glycodendrimers as Anti-Adhesion Drugs Against Type 1 Fimbriated *E. coli* Uropathogenic Infections", Mini Rev Med Chem., 7(12):1270-83, (2007).
Touaibia, M. et al., "Mannosylated G(0) Dendrimers with Nanomolar Affinities to *Escherichia coli* FimH", ChemMedChem., 2(8):1190-1201, (2007).
Touaibia, M. et al., "Tri- and Hexavalent Mannoside Clusters as Potential Inhibitors ofType 1 Fimbriated Bacteria Using Pentaerythritol and Triazole Linkages", Chem Commun., (4):380-2, (2007).
Walter, M. et al., "A Modular System for the Preparation of Diazirine-Labeled Mannose Derivatives Using Thiourea Bridging", Synthesis, 6:952-8, (2006).
Wellens, A. et al., "Intervening with Urinary Tract Infections Using Anti-Adhesives Based on the Crystal Structure of the FimH-Oligomannose-3 Complex", PLoS One, 3(4):e2040, (2008).
Written Opinion and International Search Report issued in PCT/IB2019/055806, dated Oct. 16, 2019.
International Preliminary Report on Patentability issued in PCT/IB2019/055806, dated Jun. 5, 2020.

* cited by examiner

SUBSTITUTED BIPHENYL OR PHENYLHETEROARYL-MANNOSIDES AS ANTAGONISTS OF FIMH

This application is a § 371 of International Application No. PCT/EP2020/066707, filed 17 Jun. 2020, which claims the benefit of U.S. Provisional Application No. 62/863,479, filed 19 Jun. 2019.

STATEMENT REGARDING FEDERALLY SPONSORED RESEARCH OR DEVELOPMENT

This invention was made with government support under Award Number R44AI106112 awarded by the National Institute of Allergy and Infectious Diseases of the National Institutes of Health. The government has certain rights in the invention.

FIELD OF THE INVENTION

Disclosed herein are new O-mannoside compounds and compositions and their application as pharmaceuticals for the treatment of human disease. Methods of inhibition of FimH activity in a human subject are also provided for the treatment diseases such as urinary tract infection.

BACKGROUND OF THE INVENTION

Urinary tract infection (UTI) is one of the most common infectious diseases in women. The morbidity and economic impact are enormous, with over $2.5 billion spent annually on treatment. Further, recurrent infections are a significant problem despite appropriate antibiotic therapy of the initial infection case. Women who present with an initial episode of acute UTI have a 25-44% chance of developing a second and a 3% chance of experiencing three episodes within six months of the initial UTI. Furthermore, resistance to antibiotics commonly prescribed to treat or prevent UTI is spreading rapidly among uropathogens, highlighting the need for new antibiotic-sparing and -enabling therapies.

Greater than 85% of UTI are caused by uropathogenic *Escherichia coli* (UPEC). Gram-negative bacteria such as UPEC are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone-usher pathway). Animal models of UTI have revealed that the mannose-binding FimH adhesin of type 1 pili is critical for the colonization of and invasion into the bladder epithelium by UPEC, as well as other uropathogenic members of the Enterobacteriaceae family, such as *Klebsiella, Enterobacter*, and *Citrobacter* species.

Type 1 pili are anchored in the bacterial outer membrane and are largely composed of repeating FimA protein subunits which form a helically wound cylinder that comprises the thick pilus rod. The distal FimH adhesin protein is connected to the pilus rod by the flexible tip fibrillum, which is composed of one copy each of FimF and FimG. The adhesin tip protein FimH is a two-domain protein comprised of a pilin domain (FimH$_P$), which allows it to incorporate into the pilus, and a lectin domain (FimH$_L$) that contains a conserved mannose binding pocket. The X-ray crystal structure of FimH bound to mannose showed that mannose is bound in a negatively charged pocket on FimH. The mannose binding site is highly conserved as it is invariant in 300 fimH genes sequenced from clinical UPEC strains. It is the interaction of FimH with mannosylated host proteins that is believed to mediate colonization of the lower urinary tract by UPEC and other Enterobacteriaceae during UTI.

To elucidate the molecular details of UPEC pathogenesis, several murine models of infection have been established which recapitulate many of the clinical manifestations often seen in humans. These models include acute UPEC infections, chronic and/or recurrent infections, and catheter-associated UTI. In all of these models the adhesin FimH has been shown to play an integral role in pathogenesis, highlighting it as an excellent therapeutic target. The fundamental interaction between FimH and the host is believed to occur with binding to high-mannose containing glycans, such as uroplakins and other proteins expressed on the surface of bladder epithelial cells, that coat the luminal surface of the bladder. This initial binding facilitates bacterial colonization of the bladder epithelium and invasion of the bacteria into the bladder epithelial cells. Once internalized, a single bacterium that escapes into the host cell cytoplasm can rapidly replicate and progress to form a biofilm-like intracellular bacterial community (IBC). Once these communities reach maturation they are able to disperse and escape from the cell, filamenting to evade neutrophil phagocytosis. These filamentous bacteria can then go on to infect neighboring cells, reinitiating IBC formation and the pathogenic cycle. Importantly, evidence of IBCs and bacterial filaments has been observed in the urine of women suffering with an acute UTI, supporting the validity of the mouse model in recapitulating human disease.

In contrast to UTI, which is primarily mediated by a bacterial pathogen, the disease manifested in patients suffering from idiopathic inflammatory bowel disease (IBD), such as Crohn's disease (CD) and ulcerative colitis (UC), is the result of a complex interplay between a genetically susceptible host, a dysfunctional immune system, and a microbial component. Examination of biopsied tissue from patients suffering from CD and UC has highlighted an increase in the abundance of *E. coli* associated with gut mucosa. Analysis of these bacteria has resulted in discovery of a distinct pathotype known as adherent and invasive *E. coli* (AIEC), though a portion of these strains appear similar genomically to UPEC. Identification of AIEC and their putative role in CD and UC has led to several follow up studies by several independent groups examining the intestinal microbiota in patients with IBD. This work has provided substantial evidence for the overgrowth of AIEC in ileal CD patients, with less convincing data for other IBD subtypes, including UC, colonic CD, and ileocolonic CD. Analysis of ileal enterocytes isolated from CD patients identified abnormal expression of the host receptor carcinoembryonic antigen-related cell adhesion molecule 6 (CEACAM6), which is highly mannosylated and been demonstrated to facilitate binding of AIEC to these cells via type 1 pili. Interestingly, adherence and invasion of AIEC into intestinal epithelial cells leads to increased expression of the receptor CEACAM6, suggesting AIEC can promote their own colonization of the ileum in CD patients. Utilization of a transgenic mouse expressing human CEA family gene cluster, including CEACAM6, results in increased colonization of AIEC, which recapitulates many of the clinical symptoms of CD including severe colitis, weight loss, and in this model decreased survival. Furthermore, these symptoms can be completely abolished through the administration of an anti-CEACAM6 antibody or through the genetic deletion of FimH in the bacterial strain, demonstrating a direct link between the recognition of CECAM6 by FimH and disease progression. Therefore, therapies targeting FimH among AIEC could have great benefit in relieving symptoms in CD patients.

SUMMARY OF THE INVENTION

Novel compounds and pharmaceutical compositions, which have been found to inhibit FimH have been discovered, together with methods of synthesizing and using the compounds including methods for the treatment of FimH-mediated diseases in a patient by administering the compounds.

More specifically, in one embodiment, the present invention relates to a compound of formula I, or a pharmaceutically acceptable salt thereof

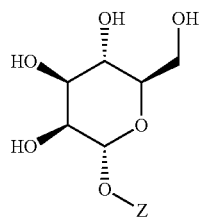

I in which
Z is

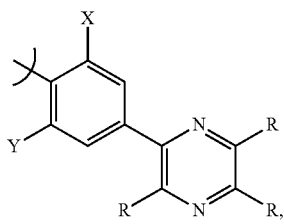

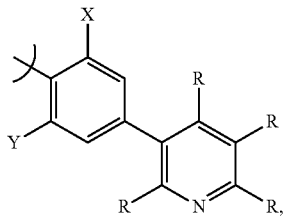

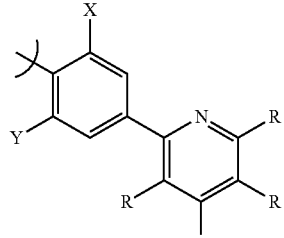

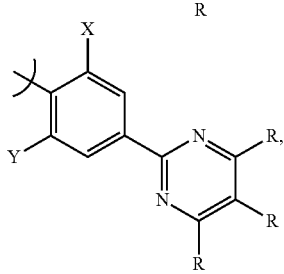

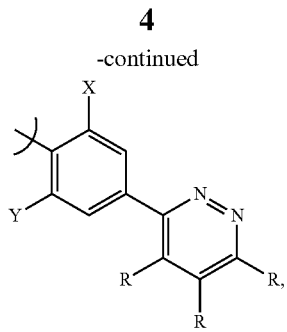

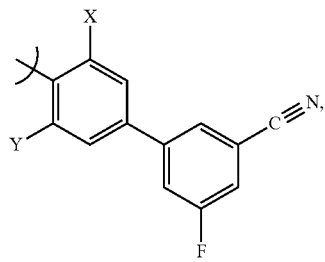

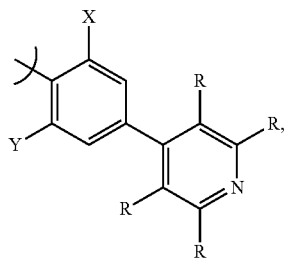

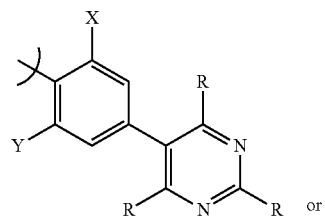

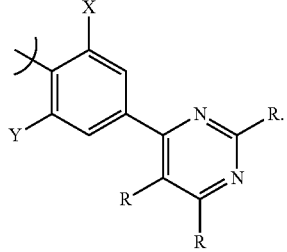 or

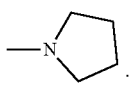

wherein
X is $CH_3$, Cl, or $CF_3$;
Y is H or F; and
each R is independently selected from the group consisting of hydrogen, CN, F, $C_{3-6}$cycloalkyl, $C_{1-6}$alkyl, —N($C_{1-6}$alkyl)$_2$, —O$C_{1-6}$alkyl, $CF_3$, and

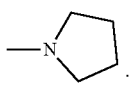.

In one embodiment, Z is:
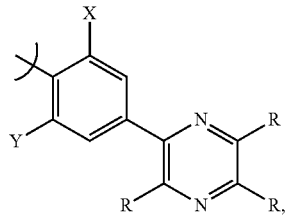
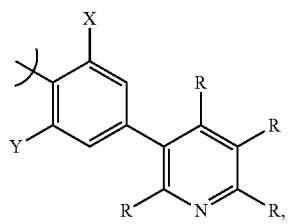
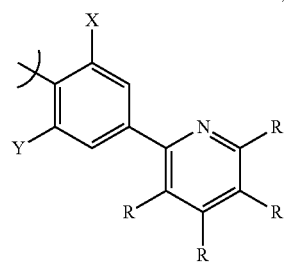
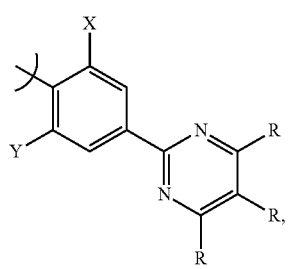
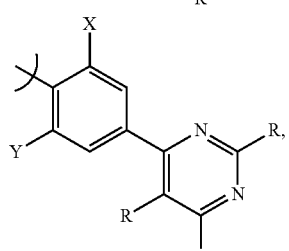
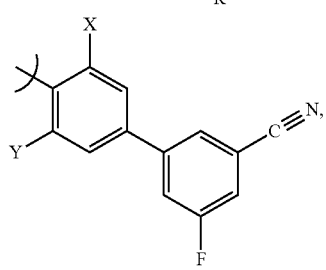
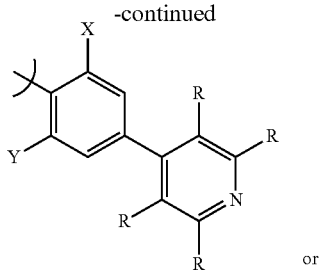
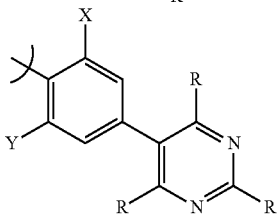
or
wherein X and Y and R are as defined herein.
In one embodiment, the invention provides a compound of Formula I, or a pharmaceutically acceptable salt thereof,
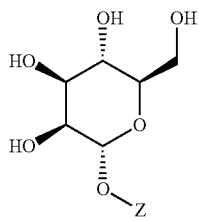
I
in which
Z is
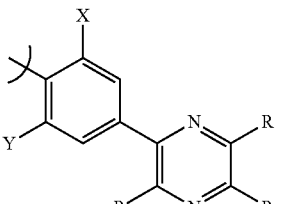
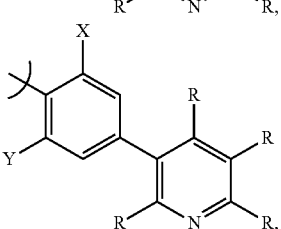
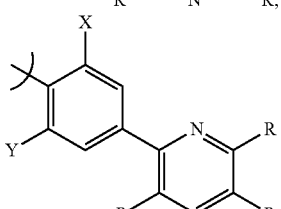

-continued
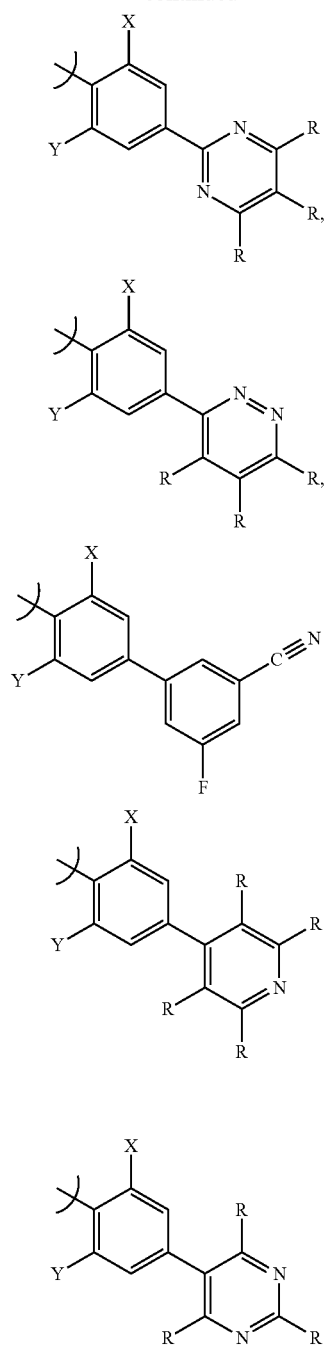
wherein
  X is CH₃, Cl, or CF₃;
  Y is H or F; and
  R is hydrogen, CN, F, $C_{3-6}$cycloalkyl, $C_{1-6}$alkyl, —N($C_{1-6}$alkyl)₂, —O$C_{1-6}$alkyl, CF₃, or
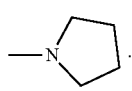
In one embodiment, Z is:
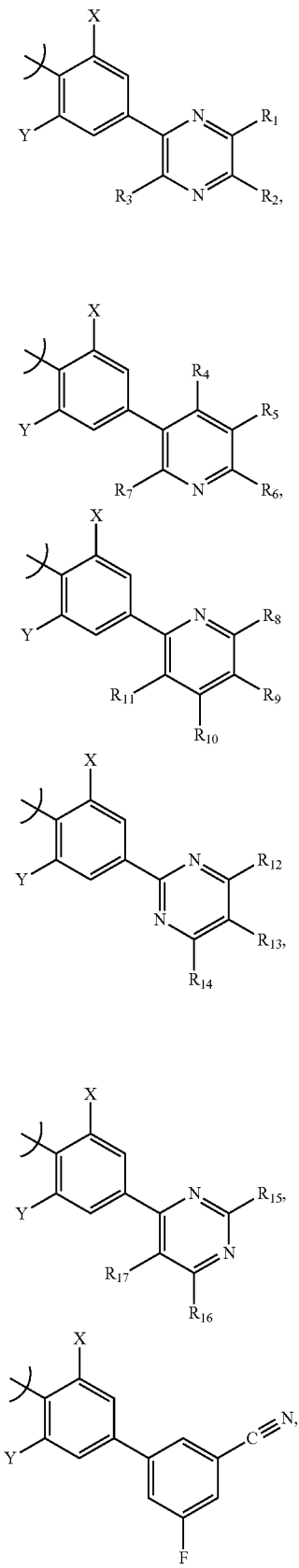

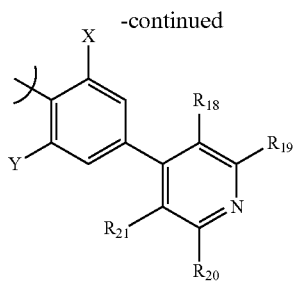

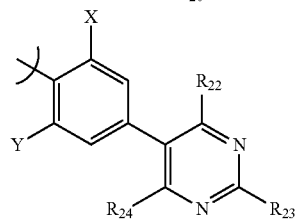

wherein X and Y are defined herein and wherein each of $R_1$ to $R_{24}$ are independently selected from the group consisting of hydrogen, CN, F, $C_{3-6}$cycloalkyl, $C_{1-6}$alkyl, —N($C_{1-6}$alkyl)$_2$, —O$C_{1-6}$alkyl, $CF_3$, and

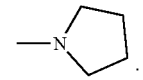

In one embodiment, Z is

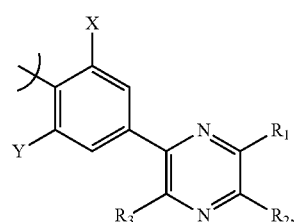

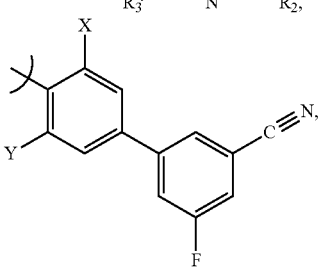

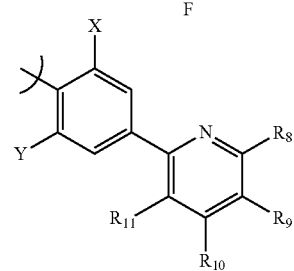

wherein X and Y are defined herein and wherein each of $R_1$, $R_2$, $R_3$, $R_8$, $R_9$, $R_{10}$ and $R_{11}$ are independently selected from the group consisting of hydrogen, CN, F, $C_{3-6}$cycloalkyl, $C_{1-6}$ alkyl, —N($C_{1-6}$alkyl)$_2$, —O$C_{1-6}$alkyl, $CF_3$, and

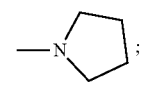

In particular embodiments, either:
X is $CH_3$ and Y is H; or
X is $CF_3$ and Y is F or H; or
X is Cl and Y is H.
In particular embodiments, either:
X is $CH_3$ and Y is H; or
X is $CF_3$ and Y is F or H.
In particular embodiments, X is $CH_3$ and Y is H.
In one embodiment, Z is:

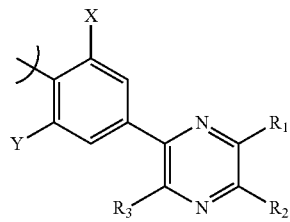

wherein X and Y are as defined herein and wherein one of $R_1$, $R_2$ and $R_3$ are selected from the group consisting of CN, F, $C_{3-6}$cycloalkyl, $C_{1-6}$alkyl, —N($C_{1-6}$alkyl)$_2$, —O$C_{1-6}$alkyl, $CF_3$, and

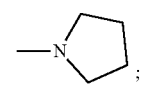

and the others are hydrogen.
In one embodiment, one of $R_1$, $R_2$ and $R_3$ are selected from the group consisting of CN, F, cyclopropyl, —$CH_3$, —N($CH_3$)$_2$, —O$CH_3$, $CF_3$, and

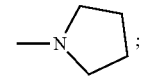

and the others are hydrogen.
In one embodiment, one of $R_1$, $R_2$ and $R_3$ are selected from the group consisting of cyclopropyl, —$CH_3$, $CF_3$, and

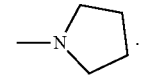

and the others are hydrogen.
In one embodiment, $R_1$ and $R_3$ are both hydrogen and $R_2$ is selected from the group consisting of cyclopropyl, —$CH_3$, $CF_3$, and In one embodiment, $R_1$ and $R_3$ are both hydrogen and $R_2$ is selected from the group consisting of cyclopropyl and $CF_3$. In one embodiment, $R_1$ and $R_3$ are both hydrogen and $R_2$ is $CF_3$.

In an alternative embodiment, Z is:

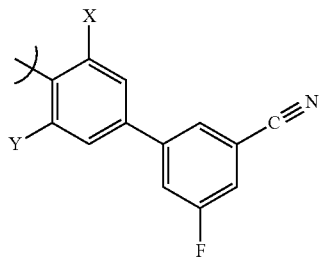

wherein X and Y are as defined herein.

In an alternative embodiment, Z is.

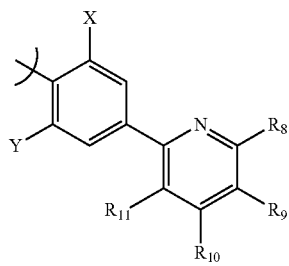

wherein X and Y are as defined herein and wherein one or two of $R_8$, $R_9$, $R_{10}$ and $R_{11}$ are selected from the group consisting of CN, F, $C_{3-6}$cycloalkyl, $C_{1-6}$alkyl, —$N(C_{1-6}$ alkyl$)_2$, —$OC_{1-6}$ alkyl, $CF_3$, and

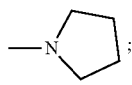

and the others are hydrogen.

In one embodiment, one or two of $R_8$, $R_9$, $R_{10}$ and $R_{11}$ are selected from the group consisting of CN, F, cyclopropyl, —$CH_3$, —$N(CH_3)_2$, —$OCH_3$, $CF_3$, and

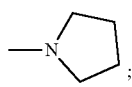

and the others are hydrogen. In a more particular embodiment, one of $R_8$, $R_9$, $R_{10}$ and $R_{11}$ are selected from the group consisting of CN, F, cyclopropyl, —$CH_3$, —$N(CH_3)_2$, —$OCH_3$, $CF_3$, and

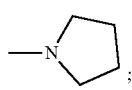

and the others are hydrogen.

In one embodiment, one or two of $R_8$, $R_9$, $R_{10}$ and $R_{11}$ are selected from the group consisting of F and $CF_3$; and the others are hydrogen. In a more particular embodiment, one of $R_8$, $R_9$, $R_{10}$ and $R_{11}$ is selected from the group consisting of F and $CF_3$; and the others are hydrogen. In a more particular embodiment one of $R_8$, $R_9$, $R_{10}$ and $R_{11}$ is $CF_3$; and the others are hydrogen. In a particular embodiment, $R_9$ is $CF_3$ and $R_8$, $R_{10}$ and $R_{11}$ are H. In another embodiment, $R_{10}$ is $CF_3$ and $R_8$, $R_9$ and $R_{11}$ are H.

In an alternative embodiment, Z is:

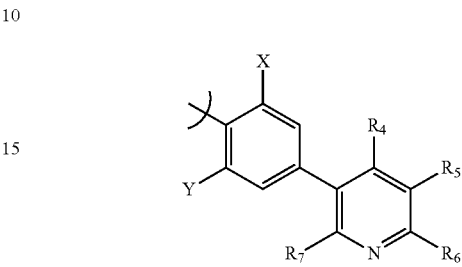

wherein X and Y are as defined herein and wherein one or two of $R_4$, $R_5$, $R_6$ and $R_7$ are selected from the group consisting of CN, F, $C_{3-6}$cycloalkyl, $C_{1-6}$alkyl, —$N(C_{1-6}$ alkyl$)_2$, —$OC_{1-6}$ alkyl, $CF_3$, and

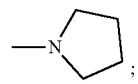

and the others are hydrogen.

In one embodiment, one or two of $R_4$, $R_5$, $R_6$ and $R_7$ are selected from the group consisting of CN, F, cyclopropyl, —$CH_3$, —$N(CH_3)_2$, —$OCH_3$, $CF_3$, and

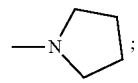

and the others are hydrogen.

In one embodiment, one or two of $R_4$, $R_5$, $R_6$ and $R_7$ are selected from the group consisting of CN, F, —$OCH_3$, $CF_3$, and

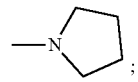

and the others are hydrogen.

In one embodiment, $R_6$ is selected from the group consisting of CN, F, —$OCH_3$, $CF_3$, and

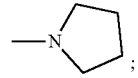

and $R_4$, $R_5$ and $R_7$ are hydrogen. In a more particular embodiment, $R_6$ is selected from the group consisting of —$OCH_3$, $CF_3$, and

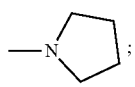

and $R_4$, $R_5$ and $R_7$ are hydrogen.

In an alternative embodiment, $R_5$ is selected from the group consisting of CN, F, —OCH$_3$, CF$_3$, and

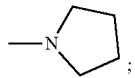

and $R_4$, $R_6$ and $R_7$ are hydrogen. In one embodiment, $R_5$ is CN and $R_4$, $R_6$ and $R_7$ are hydrogen.

In an alternative embodiment, Z is:

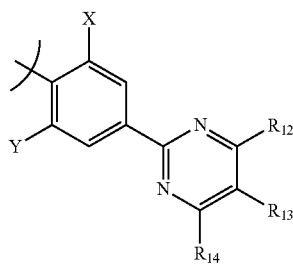

wherein X and Y are as defined herein and wherein one of $R_{12}$, $R_{13}$ and $R_{14}$ is selected from the group consisting of CN, F, $C_{3-6}$cycloalkyl, $C_{1-6}$alkyl, —N($C_{1-6}$alkyl)$_2$, —O$C_{1-6}$alkyl, CF$_3$, and

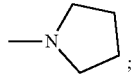

and the others are hydrogen.

In one embodiment, one of $R_{12}$, $R_{13}$ and $R_{14}$ is selected from the group consisting of CN, F, cyclopropyl, —CH$_3$, —N(CH$_3$)$_2$, —OCH$_3$, CF$_3$, and

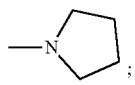

and the others are hydrogen.

In one embodiment, one of $R_{12}$, $R_{13}$ and $R_{14}$ is CF$_3$ and the others are hydrogen. In a more particular embodiment, $R_{12}$ is CF$_3$ and $R_{13}$ and $R_{14}$ are hydrogen. In another embodiment, $R_{13}$ is CF$_3$ and $R_{12}$ and $R_{14}$ are hydrogen.

In an alternative embodiment, Z is:

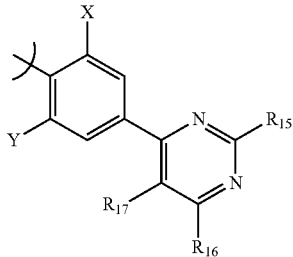

wherein X and Y are as defined herein and wherein one of $R_{15}$, $R_{16}$ and $R_{17}$ is selected from the group consisting of CN, F, $C_{3-6}$cycloalkyl, $C_{1-6}$alkyl, —N($C_{1-6}$alkyl)$_2$, —O$C_{1-6}$alkyl, CF$_3$, and

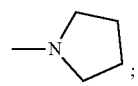

and the others are hydrogen.

In one embodiment, one of $R_{15}$, $R_{16}$ and $R_{17}$ is selected from the group consisting of CN, F, cyclopropyl, —CH$_3$, —N(CH$_3$)$_2$, —OCH$_3$, CF$_3$, and

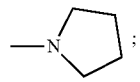

and the others are hydrogen. In a more particular embodiment, one of $R_{15}$, $R_{16}$ and $R_{17}$ is CF$_3$, and the others are hydrogen. In one embodiment, $R_{15}$ is CF$_3$, and $R_{16}$ and $R_{17}$ are hydrogen.

In an alternative embodiment, Z is:

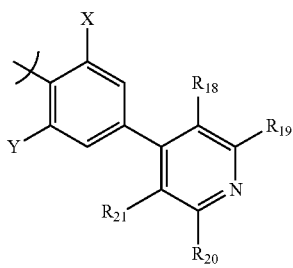

wherein X and Y are as defined herein and wherein one of $R_{18}$, $R_{19}$, $R_{20}$ and $R_{21}$ is selected from the group consisting of CN, F, $C_{3-6}$cycloalkyl, $C_{1-6}$alkyl, —N($C_{1-6}$alkyl)$_2$, —O$C_{1-6}$alkyl, CF$_3$, and

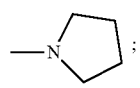

and the others are hydrogen.

In one embodiment, one of $R_{18}$, $R_{19}$, $R_{20}$ and $R_{21}$ is selected from the group consisting of CN, F, cyclopropyl, —CH$_3$, —N(CH$_3$)$_2$, —OCH$_3$, CF$_3$, and

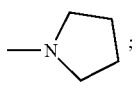

and the others are hydrogen. In a more particular embodiment, one of $R_{18}$, $R_{19}$, $R_{20}$ and $R_{21}$ is selected from the group consisting of —N(CH$_3$)$_2$ and CF$_3$; and the others are hydrogen. In one embodiment, $R_{19}$ is selected from the group consisting of —N(CH$_3$)$_2$ and CF$_3$; and $R_{18}$, $R_{20}$ and $R_{21}$ are hydrogen.

In an alternative embodiment, Z is:

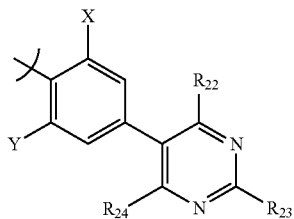

wherein X and Y are as defined herein and wherein one of $R_{22}$, $R_{23}$ and $R_{24}$ is selected from the group consisting of CN, F, $C_{3-6}$cycloalkyl, $C_{1-6}$alkyl, —N(C$_{1-6}$alkyl)$_2$, —OC$_{1-6}$alkyl, CF$_3$, and

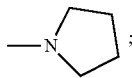

and the others are hydrogen.

In one embodiment, one of $R_{22}$, $R_{23}$ and $R_{24}$ is selected from the group consisting of CN, F, cyclopropyl, —CH$_3$, —N(CH$_3$)$_2$, —OCH$_3$, CF$_3$, and

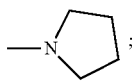

and the others are hydrogen. In a more particular embodiment, one of $R_{22}$, $R_{23}$ and $R_{24}$ is CF$_3$ and the others are hydrogen. In one embodiment, $R_{23}$ is CF$_3$ and $R_{22}$ and $R_{24}$ are hydrogen.

In one embodiment the present invention provides a compound of Formula (I) selected from the group consisting of
(2R,3S,4S,5S,6R)-2-(Hydroxymethyl)-6-(2-methyl-4-(5-(trifluoromethyl)pyrazin-2-yl)phenoxy)tetrahydro-2H-pyran-3,4,5-triol;
(2R,3S,4S,5S,6R)-2-(2-Fluoro-6-(trifluoromethyl)-4-(5-(trifluoromethyl)pyrazin-2-yl)phenoxy)-6-(hydroxymethyl) tetrahydro-2H-pyran-3,4,5-triol;
(2R,3S,4S,5S,6R)-2-(Hydroxymethyl)-6-(2-(trifluoromethyl)-4-(5-(trifluoromethyl)pyrazin-2-yl)phenoxy)tetrahydro-2H-pyran-3,4,5-triol;
5-Fluoro-3'-methyl-4'-(((2R,3S,4S,5S,6R)-3,4,5-trihydroxy-6-(hydroxymethyl)tetrahydro-2H-pyran-2-yl)oxy)-[1,1'-biphenyl]-3-carbonitrile; or
(2R,3S,4S,5S,6R)-2-(hydroxymethyl)-6-(2-methyl-4-(4-(trifluoromethyl)pyridin-2-yl)phenoxy)tetrahydro-2H-pyran-3,4,5-triol, or a pharmaceutically acceptable salt thereof.

In one embodiment the present invention provides (2R,3S,4S,5S,6R)-2-(hydroxymethyl)-6-(2-methyl-4-(5-(trifluoromethyl)pyrazin-2-yl)phenoxy)tetrahydro-2H-pyran-3,4,5-triol or a pharmaceutically acceptable salt thereof.

In one embodiment the present invention provides (2R,3S,4S,5S,6R)-2-(2-fluoro-6-(trifluoromethyl)-4-(5-(trifluoromethyl)pyrazin-2-yl)phenoxy)-6-(hydroxymethyl)tetrahydro-2H-pyran-3,4,5-triol or a pharmaceutically acceptable salt thereof.

In one embodiment the present invention provides (2R,3S,4S,5S,6R)-2-(hydroxymethyl)-6-(2-(trifluoromethyl)-4-(5-(trifluoromethyl)pyrazin-2-yl)phenoxy)tetrahydro-2H-pyran-3,4,5-triol or a pharmaceutically acceptable salt thereof.

In one embodiment the present invention provides 5-fluoro-3'-methyl-4'-(((2R,3S,4S,5S,6R)-3,4,5-trihydroxy-6-(hydroxymethyl)tetrahydro-2H-pyran-2-yl)oxy)-[1,1'-biphenyl]-3-carbonitrile or a pharmaceutically acceptable salt thereof.

In one embodiment the present invention provides (2R,3S,4S,5S,6R)-2-(hydroxymethyl)-6-(2-methyl-4-(4-(trifluoromethyl)pyridin-2-yl)phenoxy)tetrahydro-2H-pyran-3,4,5-triol or a pharmaceutically acceptable salt thereof.

In another embodiment, the present invention provides use as a medicament of a compound of formula I or a pharmaceutically acceptable salt.

In another embodiment, the present invention provides a compound of formula I or a pharmaceutically acceptable salt thereof for use in therapy.

In another embodiment, the present invention provides a compound of formula I or a pharmaceutically acceptable salt thereof for use in the treatment of a FimH binding mediated disease or condition (a disease or condition ameliorated by the inhibition of FimH binding, function or activity).

In another embodiment, the present invention provides a compound of formula I or a pharmaceutically acceptable salt thereof for use in the treatment of or prevention of a bacterial infection, Crohn's disease (CD), or Inflammatory Bowel Disease (IBD). In another embodiment, the present invention provides a compound of formula I or a pharmaceutically acceptable salt thereof for use in the treatment of a bacterial infection, Crohn's disease (CD), or Inflammatory Bowel Disease (IBD).

In another embodiment, the present invention provides a compound of formula I or a pharmaceutically acceptable salt thereof for use in the treatment or prevention of a urinary tract infection (UTI, including cystitis (bladder) and pyelonephritis infections). In another embodiment, the present invention provides a compound of formula I or a pharmaceutically acceptable salt thereof for use in the treatment of a urinary tract infection (UTI, including cystitis (bladder) and pyelonephritis infections).

In another embodiment, the present invention provides use of a compound of formula I or a pharmaceutically acceptable salt thereof in the manufacture of a medicament for the prevention or treatment of a disease or condition ameliorated by the inhibition of FimH function or activity (a disease or condition ameliorated by the inhibition of FimH binding, function or activity).

In another embodiment, the present invention provides use of a compound of formula I or a pharmaceutically acceptable salt thereof for use in the treatment or prevention of a bacterial infection, Crohn's disease (CD), or Inflammatory Bowel Disease (IBD). In one embodiment, the present invention provides use of a compound of formula I or a pharmaceutically acceptable salt thereof for use in the treatment of a bacterial infection, Crohn's disease (CD), or Inflammatory Bowel Disease (IBD).

In another embodiment, the present invention provides a method for the treatment of a FimH-mediated disease comprising the administration of a therapeutically effective amount of a compound of formula I or a pharmaceutically acceptable salt to a human patient in need thereof.

In another embodiment, the present invention provides a method for the treatment of a bacterial infection, Crohn's disease (CD), or Inflammatory Bowel Disease (IBD) with a compound of formula I or a pharmaceutically acceptable salt thereof.

In an embodiment, said bacterial infection is an antibiotic-resistant bacterial infection.

In an embodiment, said bacterial infection is a urinary tract infection (UTI).

In an embodiment, said urinary tract infection is recurrent.

In an embodiment, said urinary tract infection is chronic.

In one embodiment, the urinary tract infection is cystitis (bladder) and pyelonephritis infections.

In an embodiment, said disease is Crohn's disease.

In an embodiment, said disease is Inflammatory Bowel Disease.

In another embodiment, the present invention provides a pharmaceutical composition comprising a compound of formula I or a pharmaceutically acceptable salt thereof together with a pharmaceutically acceptable carrier.

In an embodiment, said pharmaceutical composition is formulated for oral (PO) administration.

In an embodiment, said pharmaceutical composition for oral administration is chosen from a liquid, tablet and a capsule.

In an embodiment, said pharmaceutical composition is formulated for topical administration.

In another embodiment, the present invention provides a method of treating a FimH-mediated disease comprising the step of administering:
  a. a therapeutically effective amount of a compound of formula I or a pharmaceutically acceptable salt thereof, and
  b. another therapeutic agent.

In another embodiment, the present invention provides a combination of a compound of formula I or a pharmaceutically acceptable salt and another therapeutic agent.

DETAILED DESCRIPTIONS

Definitions

The term "$C_{1-6}$ alkyl," as used herein, alone or in combination, refers to a straight-chain or branched-chain alkyl radical containing from 1 to 6 carbon atoms. Examples of $C_{1-6}$ alkyl radicals include methyl (Me), ethyl (Et), n-propyl, isopropyl, n-butyl, isobutyl, sec-butyl, tert-butyl, pentyl, iso-amyl, hexyl, and the like.

The term "$C_{3-6}$cycloalkyl," as used herein, alone or in combination, refers to a saturated monocyclic alkyl group wherein each cyclic moiety contains from 3 to 6 carbon atom ring members. The examples are cyclopropyl (cPr), cyclopentyl (cPe), cyclobutyl (cBu), and cyclohexyl (cHex).

Asymmetric centers may exist in the compound of formula I. It should be understood, that the present invention covers the compounds of absolute configuration as shown in formula I.

Because of their potential use in medicine, the salts of the compounds of formula I are preferably pharmaceutically acceptable salts. Thus, reference to salts are pharmaceutically acceptable salts. 'Pharmaceutically acceptable' refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. Suitable pharmaceutically acceptable salts include those described by Berge, Bighley and Monkhouse J. Pharm. Sci (1977) 66, pp 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

When a compound of the invention is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, g-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher pKa than the free base form of the compound.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

If the compounds of this invention contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a sodium salt or a disodium salt.

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing more pure forms used in the pharmaceutical compositions.

The term "combination" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"FimH inhibitor" or "FimH antagonist", is used herein to refer to a compound that exhibits an HAI (hemagglutination inhibition assay) titer or EC>90 with respect to FimH function/activity of no more than about 100 μM and more typically not more than about 50 μM, as measured in the FimH hemagglutination assay (HA) described generally herein. "HAI titer or EC>90" is that concentration of the FimH inhibitor/antagonist which reduces the bacterial agglutination of guinea pig red blood cells by greater than 90%. Certain compounds disclosed herein have been discovered to exhibit inhibition of this FimH function/activity. In certain embodiments, compounds will exhibit an EC>90 with respect to FimH of no more than about 10 μM; in further embodiments, compounds will exhibit an EC>90 with respect to FimH of no more than about 1 μM; in yet further embodiments, compounds will exhibit an EC>90 with respect to FimH of not more than about 250 nM; in yet further embodiments, compounds will exhibit an EC>90 with respect to FimH of not more than about 100 nM in yet further embodiments, compounds will exhibit an EC>90 with respect to FimH of not more than about 50 nM in yet further embodiments, compounds will exhibit an EC>90 with respect to FimH of not more than about 10 nM, as measured in the FimH assay described herein.

The phrase "therapeutically effective" is intended to qualify the amount of active ingredients used in the treatment of a disease or disorder or on the effecting of a clinical endpoint.

As used herein, "treat" in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

While it may be possible for the compounds of the subject invention to be administered as the raw chemical, it is also possible to present them as a pharmaceutical formulation (or alternatively referred to as pharmaceutical compositions). Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier (s) must be "therapeutically acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal, inhalation, intranasal, and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. As used herein, the term "compound(s) of the invention" means a compound of formula I in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the rectum, lung, vaginal cavity, ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation. For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg. In one embodiment, a compound of the present invention is administered around 150 mg qd (once a day) or bid (twice a day).

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for urinary tract infection involving administration of one of the compounds described herein, increased therapeutic benefit may result by also providing the patient with another therapeutic agent for urinary tract infection. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating FimH-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of FimH-mediated disorders.

Specific diseases to be treated by the compounds, compositions, and methods disclosed herein include bacterial infections, Crohn's Disease, and irritable bowel syndrome (IBS). In certain embodiments, the bacterial infection is a urinary tract infection.

Besides being useful for human treatment, certain compounds and formulations disclosed herein may also be useful for veterinary treatment of companion animals, exotic animals and farm animals, including mammals, and the like. More preferred animals include horses, dogs, and cats.

Table 1 provides compounds prepared and their mass spectrometric, biological and pharmacokinetic data (in rat), if tested.

TABLE 1

| Structure | Example and/or Compound # | HAI nM | PK DNAUC h * uM | % F | Ue % | MS Spec details |
|---|---|---|---|---|---|---|
| 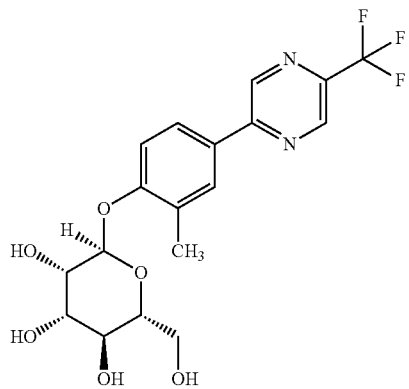 [SMILES: Cc1cc(-c2cnc(C(F)(F)F)cn2)ccc1O[C@H]1O[C@H](CO)[C@@H](O)[C@H](O)[C@@H]1O] | 1 | "++++" | "+++" | "+++" | "+++" | ESI-MS [M + H]+ Calc'd for (C18H19F3N2O6H+), 417.13, found, 417.12. |

TABLE 1-continued

| Structure | Example and/or Compound # | HAI nM | PK DNAUC h * uM | % F | Ue % | MS Spec details |
|---|---|---|---|---|---|---|
| 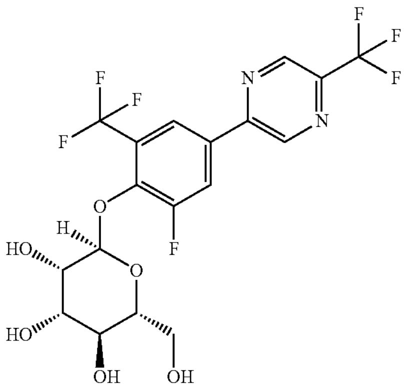 [SMILES: OC[C@H]1O[C@H](Oc2c(F)cc(-c3cnc(C(F)(F)F)cn3)cc2C(F)(F)F)[C@@H](O)[C@@H](O)[C@@H]1O] | 2 | "++++" | | | | ESI-MS [M + H]+ Calc'd for (C18H15F7N2O6H+), 489.09, found, 489.082 |
| 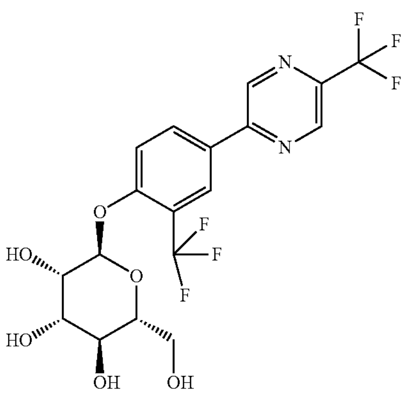 [SMILES: OC[C@H]1O[C@H](Oc2ccc(-c3cnc(C(F)(F)F)cn3)cc2C(F)(F)F)[C@@H](O)[C@@H](O)[C@@H]1O] | 3 | "+++" | "++" | | "++" | ESI-MS [M + H]+ Calc'd for (C18H16F6N2O6H+), 471.10, found, 471.091. |
| 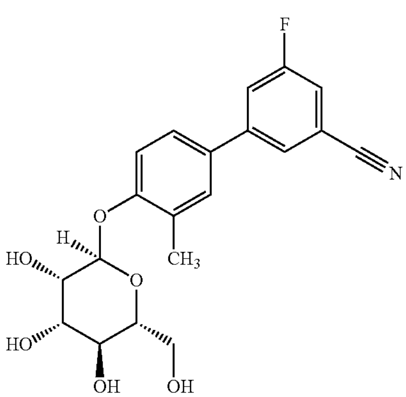 [SMILES: Cc1cc(-c2cc(F)cc(C#N)c2)ccc1O[C@H]1O[C@H](CO)[C@@H](O)[C@H](O)[C@@H]1O] | 4 | "+++" | "+++" | | "+++" | ESI-MS [M + H]+ Calc'd for (C20H20FNO6H+), 390.14, found, 390.127. |

TABLE 1-continued

| Structure | Example and/or Compound # | HAI nM | PK DNAUC h * uM | % F | Ue % | MS Spec details |
|---|---|---|---|---|---|---|
| 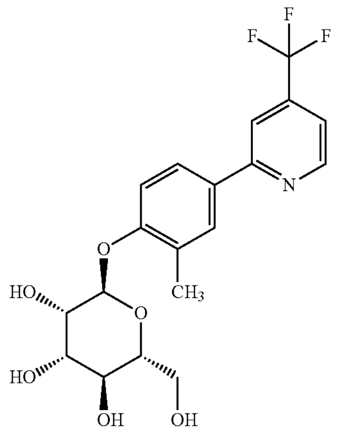 [SMILES: Cc1cc(-c2cc(C(F)(F)F)ccn2)ccc1O[C@H]1O[C@H](CO)[C@@H](O)[C@H](O)[C@@H]1O] | 5 | "+++" | "+++" | "+++" | | ESI-MS [M + H]+ Calc'd for (C19H20F3NOH+), 416.13, found, 416.124. |
| 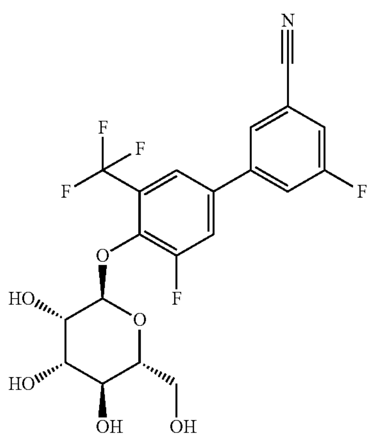 [SMILES: N#Cc1cc(F)cc(-c2cc(F)c(O[C@H]3O[C@H](CO)[C@@H](O)[C@H](O)[C@@H]3O)c(C(F)(F)F)c2)c1] | 6 | "++++" | "+" | | | ESI-MS [M + H]+ Calc'd for (C20H16F5NO6H+), 462.10, found, 462.09. |
| 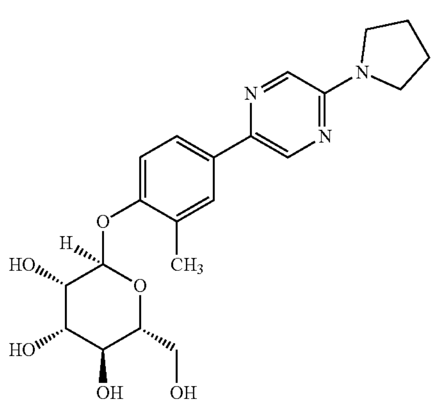 [SMILES: Cc1cc(-c2cnc(N3CCCC3)cn2)ccc1O[C@H]1O[C@H](CO)[C@@H](O)[C@H](O)[C@@H]1O] | 7 | "++++" | "+" | | | ESI-MS [M + H]+ Calc'd for (C21H27N3O6H+), 418.20, found, 418.19 |

TABLE 1-continued

| Structure | Example and/or Compound # | HAI nM | PK DNAUC h * uM | % F | Ue % | MS Spec details |
|---|---|---|---|---|---|---|
| 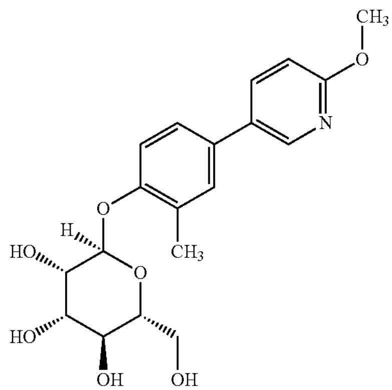 [SMILES: COc1ccc(-c2ccc(O[C@H]3O[C@H](CO)[C@@H](O)[C@H](O)[C@@H]3O)c(C)c2)cn1] | 8 | "+++" | | | | ESI-MS [M + H]+ Calc'd for (C19H23NO7H+), 378.16, found, :378.147. |
| 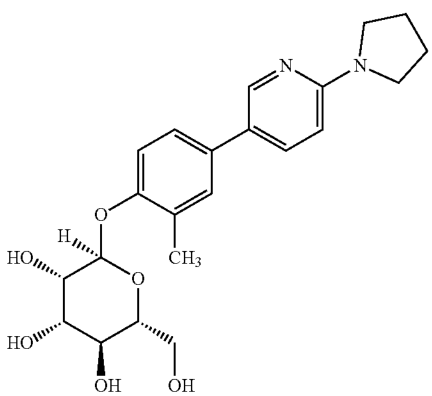 [SMILES: Cc1cc(-c2ccc(N3CCCC3)nc2)ccc1O[C@H]1O[C@H](CO)[C@@H](O)[C@H](O)[C@@H]1O] | 9 | "++++" | | | | ESI-MS [M + H]+ Calc'd for (C22H28N2O6H+), 417.20, found, 417.195. |
| 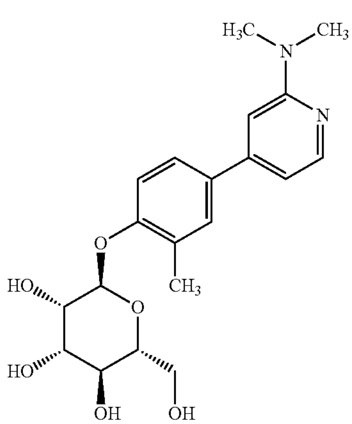 [SMILES: Cc1cc(-c2ccnc(N(C)C)c2)ccc1O[C@H]1O[C@H](CO)[C@@H](O)[C@H](O)[C@@H]1O] | 10 | "++++" | | | | ESI-MS [M + H]+ Calc'd for (C20H26N2O6H+), 391.19, found, 391.179 |

TABLE 1-continued

| Structure | Example and/or Compound # | HAI nM | PK DNAUC h * uM | % F | Ue % | MS Spec details |
|---|---|---|---|---|---|---|
| 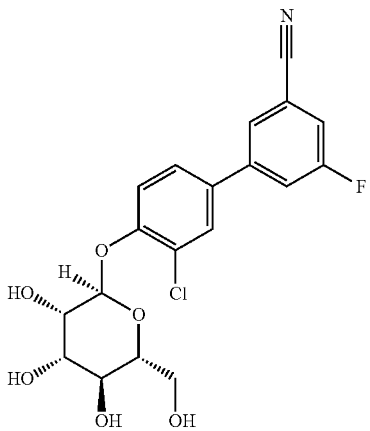 [SMILES: N#Cc1cc(F)cc(-c2ccc(O[C@H]3O[C@H](CO)[C@@H](O)[C@H](O)[C@@H]3O)c(Cl)c2)c1] | 11 | "+++" | | | | ESI-MS [M + H]+ Calc'd for (C19H17ClFNO6H+), 410.08, found, 410.073. |
| 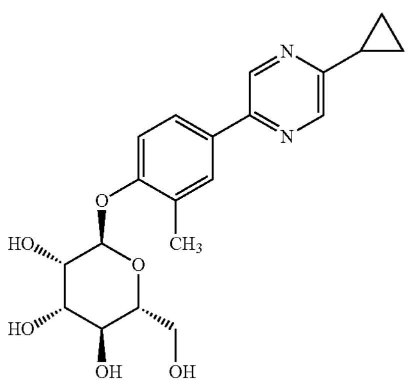 [SMILES: Cc1cc(-c2cnc(C3CC3)cn2)ccc1O[C@H]1O[C@H](CO)[C@@H](O)[C@H](O)[C@@H]1O] | 12 | "++++" | "++" | "+++" | "++" | ESI-MS [M + H]+ Calc'd for (C20H24N2O6H+), 390.17, found, 390.127. |
| 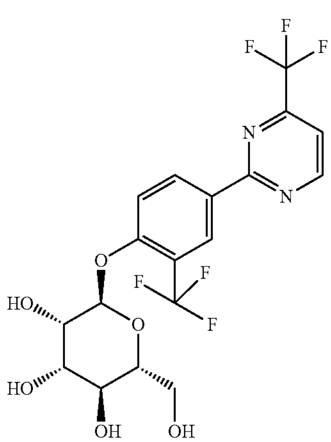 [SMILES: OC[C@H]1O[C@H](Oc2ccc(-c3nccc(C(F)(F)F)n3)cc2C(F)(F)F)[C@@H](O)[C@@H](O)[C@@H]1O] | 13 | "+++" | | | | ESI-MS [M + H]+ Calc'd for (C18H16F6N2O6H+), 471.10, found, 471.091. |

TABLE 1-continued

| Structure | Example and/or Compound # | HAI nM | PK DNAUC h * uM | % F | Ue % | MS Spec details |
|---|---|---|---|---|---|---|
| (structure 14) | 14 | "+++" | "+" | | | ESI-MS [M + H]+ Calc'd for (C18H19F3N2O6H+), 417.13, found, 417.12. |
| (structure 15) | 15 | "+++" | | | | ESI-MS [M + H]+ Calc'd for (C18H19F3N2O6H+), 417.13, found, 417.12. |
| (structure 16) | 16 | "++++" | "++" | | | ESI-MS [M + H]+ Calc'd for (C18H19F3N2O6H+), 417.13, found, 417.129. |
| (structure 17) | 17 | "+++" | | | | ESI-MS [M + H]+ Calc'd for (C20H16F5NO6H+), 363.16, found, 363.148. |

TABLE 1-continued

| Structure | Example and/or Compound # | HAI nM | PK DNAUC h * uM | % F | Ue % | MS Spec details |
|---|---|---|---|---|---|---|
| 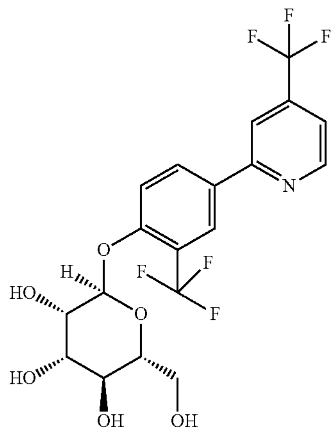 [SMILES: OC[C@H]1O[C@H](Oc2ccc(-c3cc(C(F)(F)F)ccn3)cc2C(F)(F)F)[C@@H](O)[C@@H](O)[C@@H]1O] | 18 | "+++" | | | | ESI-MS [M + H]+ Calc'd for (C19H17F6NO6H+), 470.11, found, 470.096. |
| 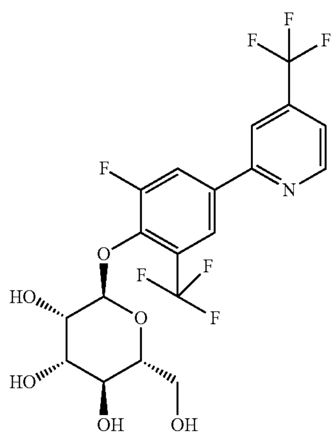 [SMILES: OC[C@H]1O[C@H](Oc2c(F)cc(-c3cc(C(F)(F)F)ccn3)cc2C(F)(F)F)[C@@H](O)[C@@H](O)[C@@H]1O] | 19 | "++++" | | | | ESI-MS [M + H]+ Calc'd for (C19H16F7NO6H+), 488.10, found, 488.087. |
| 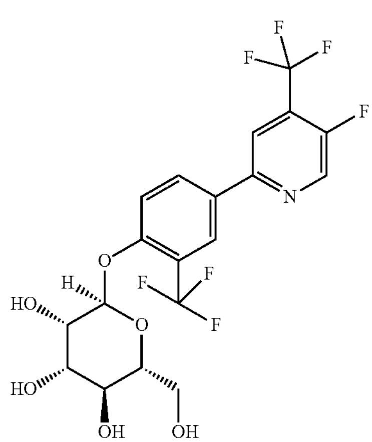 [SMILES: OC[C@H]1O[C@H](Oc2ccc(-c3cc(C(F)(F)F)c(F)cn3)cc2C(F)(F)F)[C@@H](O)[C@@H](O)[C@@H]1O] | 20 | "+++" | | | | ESI-MS [M + H]+ Calc'd for (C19H16F7NO6H+), 488.10, found, 488.087. |

TABLE 1-continued

| Structure | Example and/or Compound # | HAI nM | PK DNAUC h * uM | % F | Ue % | MS Spec details |
|---|---|---|---|---|---|---|
| 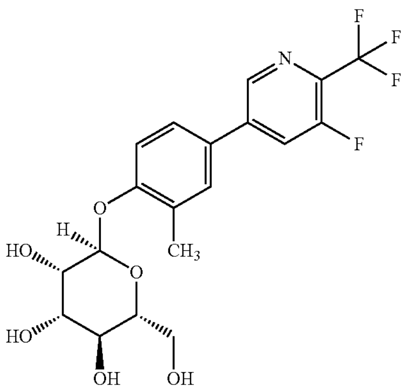 [SMILES: Cc1cc(-c2cnc(C(F)(F)F)c(F)c2)ccc1O[C@H]1O[C@H](CO)[C@@H](O)[C@H](O)[C@@H]1O] | 21 | "+++" | | | | ESI-MS [M + H]+ Calc'd for (C19H19F4NO6H+), 434.12, found, 434.115. |
| 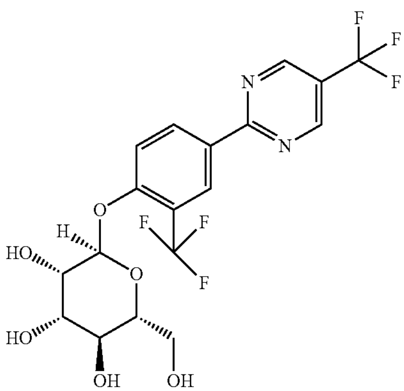 [SMILES: OC[C@H]1O[C@H](Oc2ccc(-c3ncc(C(F)(F)F)cn3)cc2C(F)(F)F)[C@@H](O)[C@@H](O)[C@@H]1O] | 22 | "+++" | | | | ESI-MS [M + H]+ Calc'd for (C18H16F6N2O6H+), 471.10, found, 471.091. |
| 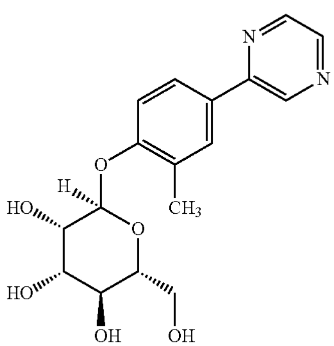 [SMILES: Cc1cc(-c2cnccn2)ccc1O[C@H]1O[C@H](CO)[C@@H](O)[C@H](O)[C@@H]1O] | 23 | "+++" | | | | ESI-MS [M + H]+ Calc'd for (C17H20N2O6H+), 349.14, found, 349.132. |
| 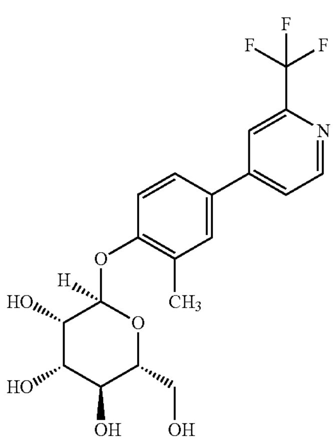 [SMILES: Cc1cc(-c2ccnc(C(F)(F)F)c2)ccc1O[C@H]1O[C@H](CO)[C@@H](O)[C@H](O)[C@@H]1O] | 24 | "+++" | | | | ESI-MS [M + H]+ Calc'd for (C19H20F3NO6H+), 416.13, found, 416.124 |

TABLE 1-continued
| Structure | Example and/or Compound # | HAI nM | PK DNAUC h * uM | % F | Ue % | MS Spec details |
|---|---|---|---|---|---|---|
| 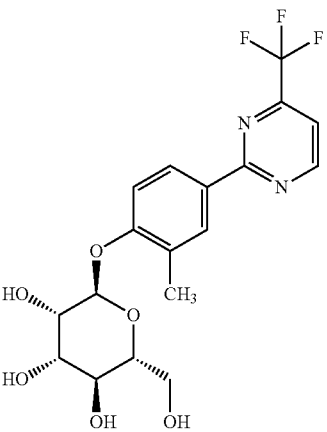 | 25 | "+++" | | | | ESI-MS [M + H]⁺ Calc'd for (C18H19F3N2O6H⁺), 417.13, found. 417.12. |
| 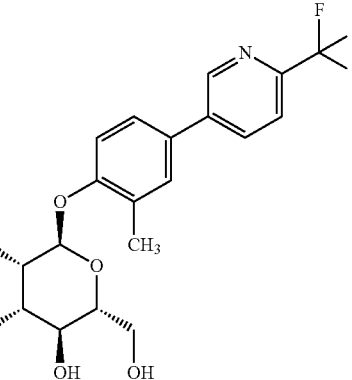 | 26 | "+++" | | | | ESI-MS [M + H]⁺ Calc'd for (C19H20F3NO6H⁺), 416.13, found, 416.124. |
| 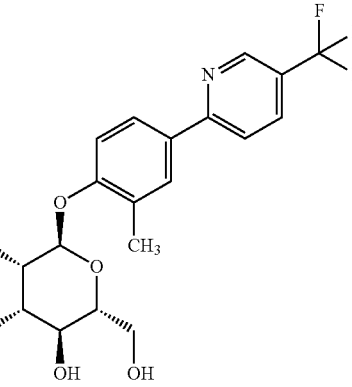 | 27 | "+++" | | | | ESI-MS [M + H]⁺ Calc'd for (C19H20F3NO6H⁺), 416.13, found, 416.124. |

TABLE 1-continued

| Structure | Example and/or Compound # | HAI nM | PK DNAUC h * uM | % F | Ue % | MS Spec details |
| --- | --- | --- | --- | --- | --- | --- |
| 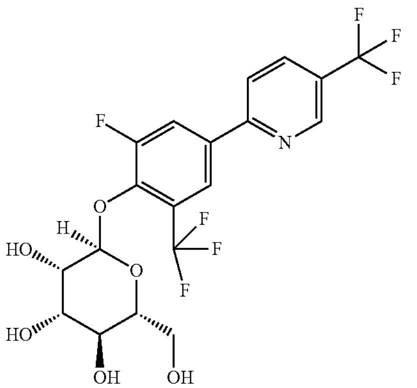 [SMILES: OC[C@H]1O[C@H](Oc2c(F)cc(-c3ccc(C(F)(F)F)cn3)cc2C(F)(F)F)[C@@H](O)[C@@H](O)[C@@H]1O] | 28 | "++++" | "+++" | "++" | | ESI-MS [M + H]+ Calc'd for (C19H16F7NO6H+), 488.10, found, 488.087. |
| 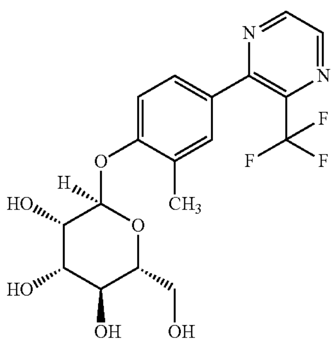 [SMILES: Cc1cc(-c2nccnc2C(F)(F)F)ccc1O[C@H]1O[C@H](CO)[C@@H](O)[C@H](O)[C@@H]1O] | 29 | "+++" | | | | ESI-MS [M + H]+ Calc'd for (C18H19F3N2O6H+), 417.13, found, 417.12. |
| 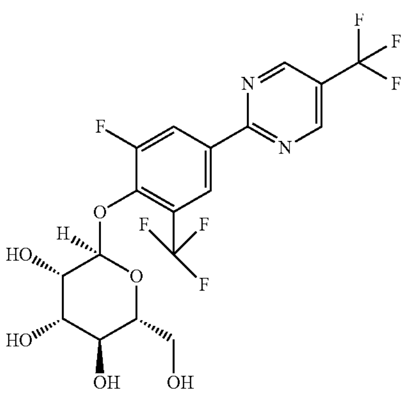 [SMILES: OC[C@H]1O[C@H](Oc2c(F)cc(-c3ncc(C(F)(F)F)cn3)cc2C(F)(F)F)[C@@H](O)[C@@H](O)[C@@H]1O] | 30 | "++++" | | | | ESI-MS [M + H]+ Calc'd for (C18H15F7N2O6H+), 489.09, found, 489.082. |
| 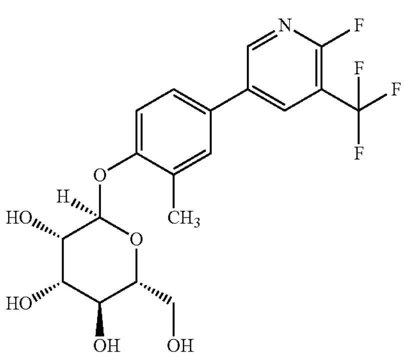 [SMILES: Cc1cc(-c2cnc(F)c(C(F)(F)F)c2)ccc1O[C@H]1O[C@H](CO)[C@@H](O)[C@H](O)[C@@H]1O] | 31 | "+++" | | | | ESI-MS [M + H]+ Calc'd for (C19H19F4NO6H+), 434.12, found, 434.115. |

TABLE 1-continued

| Structure | Example and/or Compound # | HAI nM | PK DNAUC h * uM | % F | Ue % | MS Spec details |
|---|---|---|---|---|---|---|
| 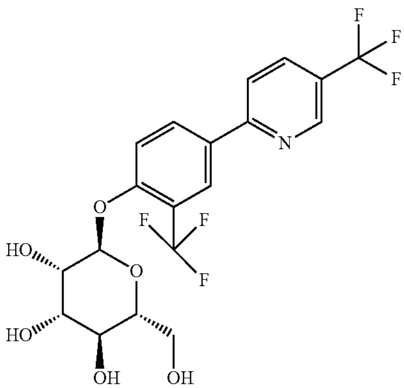 [SMILES: OC[C@H]1O[C@H](Oc2ccc(-c3ccc(C(F)(F)F)cn3)cc2C(F)(F)F)[C@@H](O)[C@@H](O)[C@@H]1O] | 32 | "+++" | | | | ESI-MS [M + H]+ Calc'd for (C19H17F6NO6H+), 470.11, found, 470.096 |
| 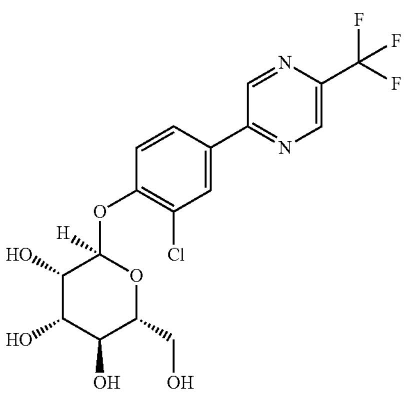 [SMILES: OC[C@H]1O[C@H](Oc2ccc(-c3cnc(C(F)(F)F)cn3)cc2Cl)[C@@H](O)[C@@H](O)[C@@H]1O] | 33 | "+++" | | | | ESI-MS [M + H]+ Calc'd for (C17H16ClF3N2O6H+), 437.07, found, 437.065. |
| 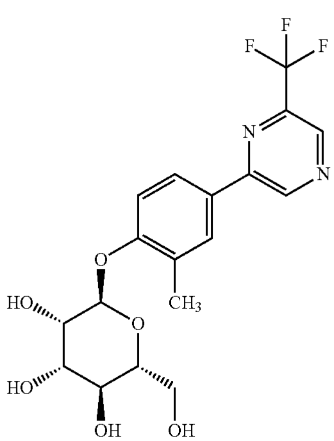 [SMILES: Cc1cc(-c2cncc(C(F)(F)F)n2)ccc1O[C@H]1O[C@H](CO)[C@@H](O)[C@H](O)[C@@H]1O] | 34 | "+++" | | | | ESI-MS [M + H]+ Calc'd for (C18H19F3N2O6H+), 417.13, found, 417.12. |

TABLE 1-continued
| Structure | Example and/or Compound # | HAI nM | PK DNAUC h * uM | % F | Ue % | MS Spec details |
|---|---|---|---|---|---|---|
| 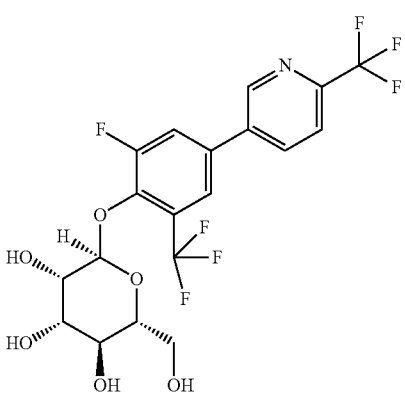 [SMILES: OC[C@H]1O[C@H](Oc2c(F)cc(-c3ccc(C(F)(F)F)nc3)cc2C(F)(F)F)[C@@H](O)[C@@H](O)[C@@H]1O] | 35 | "+++" | "+" | | | ESI-MS [M + H]+ Calc'd for (C20H16F5NO6H+), 488.10, found, 488.087 |
| 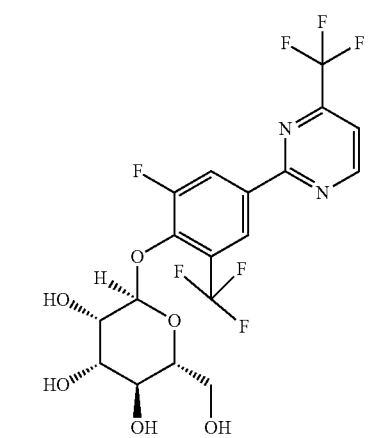 [SMILES: OC[C@H]1O[C@H](Oc2c(F)cc(-c3nccc(C(F)(F)F)n3)cc2C(F)(F)F)[C@@H](O)[C@@H](O)[C@@H]1O] | 36 | "++++" | | | | ESI-MS [M + H]+ Calc'd for (C18 H15F7N2O6H+), 489.09, found, 489.082. |
| 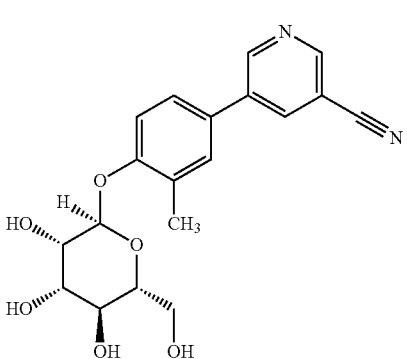 [SMILES: Cc1cc(-c2cncc(C#N)c2)ccc1O[C@H]1O[C@H](CO)[C@@H](O)[C@H](O)[C@@H]1O] | 37 | "++++" | "+" | | | ESI-MS [M + H]+ Calc'd for (C19H20N2O6H+), 373.14, found, 373.132. |

TABLE 1-continued

| Structure | Example and/or Compound # | HAI nM | PK DNAUC h * uM | % F | Ue % | MS Spec details |
|---|---|---|---|---|---|---|
| 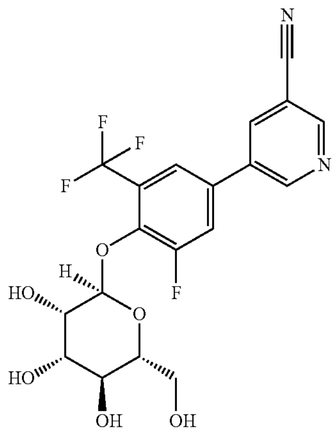 [SMILES: N#Cc1cncc(-c2cc(F)c(O[C@H]3O[C@H](CO)[C@@H](O)[C@H](O)[C@@H]3O)c(C(F)(F)F)c2)c1] | 38 | "++++" | "+" | | | ESI-MS [M + H]+ Calc'd for (C19H16F4N2O6H+), 445.10, found, 445.094. |
| 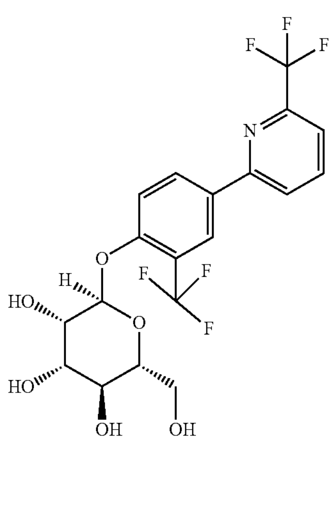 [SMILES: OC[C@H]1O[C@H](Oc2ccc(-c3cccc(C(F)(F)F)n3)cc2C(F)(F)F)[C@@H](O)[C@@H](O)[C@@H]1O] | 39 | "+++" | | | | ESI-MS [M + H]+ Calc'd for (C19H17F6NO6H+), 470.11, found, 470.096. |

TABLE 1-continued

| Structure | Example and/or Compound # | HAI nM | PK DNAUC h * uM | % F | Ue % | MS Spec details |
|---|---|---|---|---|---|---|
| [structure: 6-(trifluoromethyl)pyridine linked to methylphenyl mannoside] | 40 | "+++" | | | | ESI-MS [M + H]$^+$ Calc'd for (C19H20F3NO6H$^+$), 416.13, found, 416.124. |

Legend for Table 1
DNAUC oral
h * uM
(DN = dose normalized)    % F    Ue % po
"+"    <01 h · μM    <10%    <0.5%
"++"    0.1 ≤ x ≤ 0.2h · μM    10 ≤ x ≤ 30%    0.5 ≤ x ≤ 5%
"+++"    >0.2 h · μM    >30%    >5%
HAI nM
<50    "++++"
50-200    "+++"
201-1000    "++"
>1000    "+"

Protocols Used to Evaluate the Compounds of Invention

The activities of the Examples 1-40 compounds above as FimH antagonists/inhibitors were obtained by the following assay(s), and values are provided in Table 1. The values not provided mean that the activities have not yet been tested.

Hemagglutination Inhibition Assay (HAI)

The hemagglutination inhibition (HAI) assay was performed with UTI89 bacteria and guinea pig red blood cells, as previously described (S. J. Hultgren, W. R. Schwan, A. J. Schaeffer, J. L. Duncan Infect. Immun. 1986, 54, 613-620 and Jarvis, C.; Han, Z.; Kalas, V.; Klein, R.; Pinkner, J. S.; Ford, B.; Binkley, J.; Cusumano, C. K.; Cusumano, Z.; Mydock-McGrane, L.; Hultgren, S. J.; Janetka, J. W., ChemMedChem 2016, 11, 367-373). Results are listed in Table 2. Values not listed were not tested.

General Assays for Obtaining AUC Oral h*μm, % F, and Ue % PO Values 1.1. Animals Male Wistar Han rats were purchased from Vital River Laboratory Animal Technology Co. Ltd (Beijing, China). The animals were approx. 6-8 weeks old with body weights of 200-300 g on the dosing date. The animals were housed in a 12-hour light/12-hour dark cycle environment and had free access to food and water. All animals were fed prior to dosing. Studies were approved by the Pharmaron Institutional Animal Care and Use Committee (IACUC).

1.2. Study Design

Male Wistar Han rats (n=3 per dose group) were assigned to 1 group as shown in the table below. Test article was administered as an intravenous infusion for 1 hour (1 mg/kg) at 5 mL/kg/h. After 48 h, animals received a single oral dose (5 mg/kg, free form) at a dose volume of 10 mL/kg, respectively. Blood samples were collected at various time points after IV infusion and PO administrations. Urine samples were collected at various time points after IV infusion and PO administrations (for some compounds).

| Group | Dose Level (mg/kg) | Infusion Rate (mL/kg/h) | Dose Volume (mL/kg) | Conc. (mg/mL) | Administration Route | No. of Animals |
|---|---|---|---|---|---|---|
| 1 | 1 | 5 | — | 0.2 | IV infusion | 3/Group |
| 2 | 5 | — | 10 | 0.5 | PO | 3/Group |

1.3. Formulation Preparation

Preparation of dosing for IV infusion administration (1 mg/kg):

Test article was dissolved in DMSO with vortexing and sonification to obtain a stock solution. An aliquot of the stock solution was mixed with 10% HP-β-CD in saline with vortexing to obtain a solution with concentration at 0.2 mg/mL of test article.

Preparation of dosing for PO administration (5 mg/kg):

Test article was added into 1% Methyl Cellulose with vortexing and sonication to obtain a homogeneous suspension with concentration at 0.5 mg/mL of test article.

1.4. Sample Collection

Blood Samples:

For IV infusion (1 mg/kg) administration, blood samples were collected from each animal at 0, 0.25, 0.5, 0.75, 1, 1.08, 1.25, 1.5, 1.75, 2, 3, 5, 8, 12, 24 hour post-dose.

For PO (5 mg/kg) administration, blood samples were collected from each animal at 0, 0.25, 0.5, 1, 1.5, 2, 3, 4, 6, 8, 12, 24 hour post-dose.

Blood samples (50 μL) were collected from each animal via jugular vein. These blood samples were placed into tubes containing $K_2EDTA$. Whole blood was mixed with same volume of water and inverted several times. The blood samples were stored at −75±15° C. until analysis.

Urine Samples:

For IV infusion (1 mg/kg) administration, urine samples were collected from each animal at 0-4, 4-8, 8-12, 12-24 hour post-dose.

For PO (5 mg/kg) administration, urine samples were collected (for some compounds) from each animal at 0-4, 4-8, 8-12, 12-24 hour post-dose.

Urine samples were collected continuously into containers maintained over dry ice at the intervals outlined below and stored at −80° C. prior to analysis.

1.5. Preparation of Standard Solutions for LC-MS/MS Analysis 10 mg/mL of test article stock solution was diluted with DMSO to obtain a 1 mg/mL standard stock solution (free form).

Calibration standard working solutions were prepared at concentrations of 5, 10, 20, 50, 100, 500, 1000, 5000 and 10000 ng/mL by serial dilution of the standard stock solution in 50% acetonitrile in water. Quality control working solutions at concentrations of 10, 500 and 8000 ng/mL were prepared by serial dilution of the standard stock solution in 50% acetonitrile in water. These QC samples were prepared on the day of analysis in the same way as calibration standards.

1-6. Sample Treatment

5 μL of each calibration standard working solution (5, 10, 20, 50, 100, 500, 1000, 5000 and 10000 ng/mL) was added to 50 μL of blank Wistar Han rat blood (Blank blood: water=1:1) or urine to achieve calibration standards of 0.5-1000 ng/mL (0.5, 1, 2, 5, 10, 50, 100, 500, 1000 ng/mL) in a total volume of 55 μL. Quality Control (QC) samples at 1 ng/mL (low), 50 ng/mL (mid), 800 ng/mL (high) for blood or urine were prepared independently for those used for the calibration curves. These QC samples were prepared on the day of analysis in the same way as calibration standards.

55 μL of standards, 55 μL of QC samples or 55 μL of unknown samples (50 μL of blood or urine with 5 μL 50% acetonitrile) were mixed to 200 μL of acetonitrile containing IS (dexamethasone) to precipitate proteins. Then the samples were vortexed for 30 sec. After centrifugation at 4° C., 4700 rpm for 30 min, and 5 μL of the supernatant was injected into the LC-MS/MS system for quantitative analysis.

1.7. Pharmacokinetic Analysis

Test article blood and urine concentrations for each animal following IV infusion at 1 mg/kg and PO at 5 mg/kg were used to calculate pharmacokinetic parameters by employing a non-compartmental analysis (Phoenix™ WinNonlin® 7.0). The linear trapezoidal algorithm was used for AUC calculation.

AUC oral h*uM: Area under the curve (AUC) of drug concentration in blood vs. time (units: h*μM) following oral administration DNAUC Dose normalized area under the curve is calculate by divided the area under the curve divided by the dose in the mg/kg % F: Oral bioavailability (%) derived from the ratio of dose-normalized AUC following PO and IV administration Ue % PO: Percentage of oral dose eliminated unchanged in urine or an estimate of that parameter generated from using the percentage of the iv dose eliminated in the urine times the oral bioavailability Production Methods:

Compounds of the invention can be made following the schemes and Examples provided below.

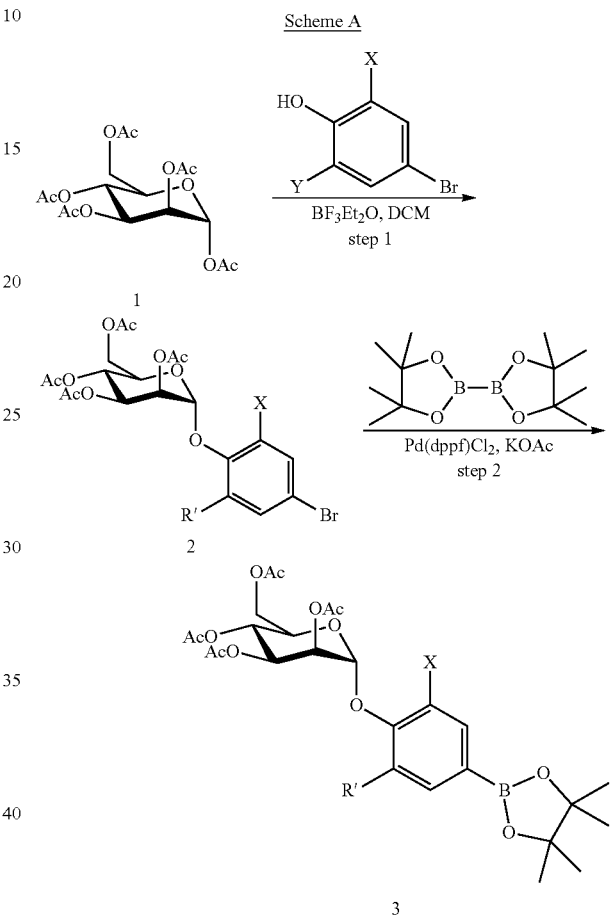

Scheme A

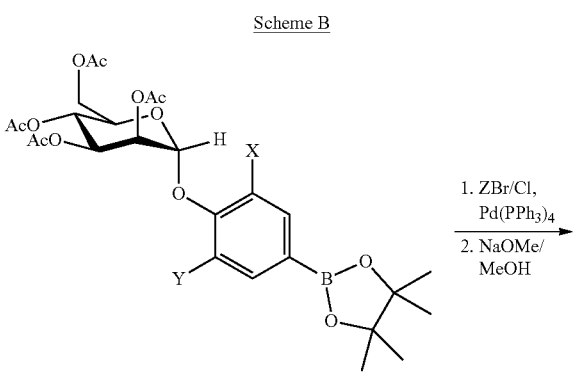

For the Example compounds, the Suzuki coupling precursors were synthesized by the route shown in scheme A to produce the aryl bromide (2) or aryl boronate (3) which were use in the subsequent schemes B and C below to afford the final compounds.

Scheme B

53

-continued

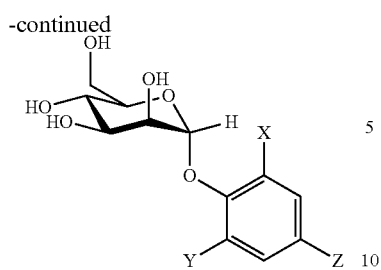

Scheme C

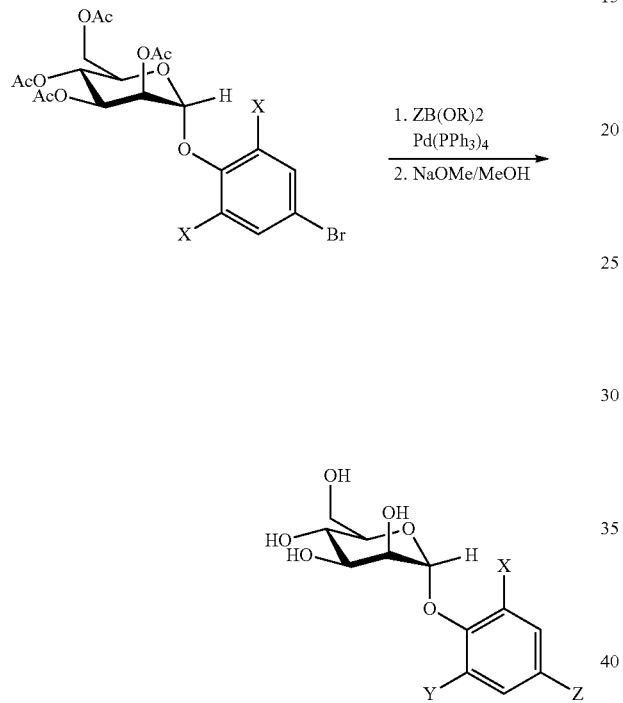

General procedure for the Suzuki Coupling reactions: To a solution of mannoside (1.0 equiv) in dioxane/water (V/V=5/1) are added aryl boronic acid (boronate) or aryl halide (1.1 equiv), cesium carbonate (3 equiv) and tetrakis(triphenylphosphine)palladium (0.05 equiv) at rt. The resulting mixture is degassed three times. The flask is then placed in an oil bath preheated to 80° C., and allowed to stir for the time specified (typically 30 min to 2 h). The reaction mixture is then cooled to rt and solvents are evaporated under reduced pressure. The crude residue is then purified by silica gel chromatography. The product is then deprotected by protocol A.

Deprotection protocol A: Unless specified otherwise, for the Example compounds, acetate protecting groups are removed by dissolving the partially purified mannoside from the Suzuki reaction into MeOH (3-5 mL), and cooling to 0° C. [1M] Sodium methoxide in MeOH is added dropwise until a pH of 9-10 is achieved. After 5 min, the ice bath is removed and the reaction mixture is stirred for the time specified. Upon completion, the reaction is quenched with water (4 drops) and concentrated under reduced pressure. The crude product is purified by Prep-HPLC with different conditions.

54

Example 1

(2R,3S,4S,5S,6R)-2-(Hydroxymethyl)-6-(2-methyl-4-(5-(trifluoromethyl)pyrazin-2-yl)phenoxy)tetrahydro-2H-pyran-3,4,5-triol

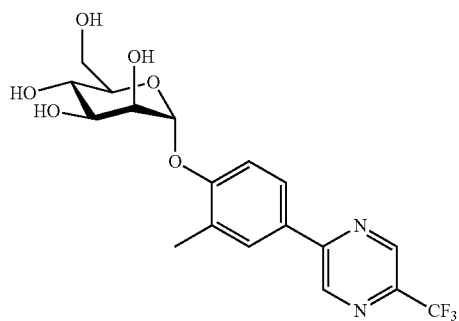

(2R,3R,4S,5S,6R)-2-(Acetoxymethyl)-6-(4-bromo-2-methylphenoxy)tetrahydro-2H-pyran-3,4,5-triyl triacetate To a solution of (2R,3S,4S,5R,6R)-6-(acetoxymethyl)tetrahydro-2H-pyran-2,3,4,5-tetrayl tetraacetate (8.0 g, 20.5 mmol) and 4-bromo-2-methylphenol (5.0 g, 26.7 mmol) in DCM (dichloromethane) (50 mL) were added $BF_3$-$Et_2O$ (10 mL, 77.5 mmol) at 25° C. The reaction mixture was stirred at 45° C. for 18 h. After completion, the reaction mixture was concentrated to get a residue. The residue was purified by silica gel column chromatography, eluting with (PE (petroleum ether):EA (ethyl acetate)=3:1) to afford the title product (5.5 g, 52% yield, 0.106 mmol) as a yellow solid. ESI-MS $[M+Na]^+$ Calc'd for $(C_{21}H_{25}BrO_{10}Na^+)$ 539.05, found 539.00.

(2R,3R,4S,5S,6R)-2-(Acetoxymethyl)-6-(2-methyl-4-(4,4,5,5-tetramethyl-1,3,2-dioxaborolan-2-yl)phenoxy)tetrahydro-2H-pyran-3,4,5-triyl triacetate To a solution of (2R,3R,4S,5S,6R)-2-(acetoxymethyl)-6-(4-bromo-2-methylphenoxy) tetrahydro-2H-pyran-3,4,5-triyl triacetate (600 mg 1.16 mmol) in dioxane (3 ml) was added 4,4,4',4',5,5,5',5'-octamethyl-2,2'-bi(1,3,2-dioxaborolane) (355 mg 1.4 mmol), Pd(dppf)Cl$_2$/DCM (95 mg 0.117 mmol) and KOAc (340 mg 3.46 mmol) at 25° C. The resulting solution was stirred for 16 h at 80° C. under $N_2$. After completion, the reaction mixture was quenched with water (10 mL) and extracted with EtOAc (3×20 mL). The combined organic layers were washed with brine (5 mL), dried over $Na_2SO_4$ and filtered. The filtrate was concentrated under reduced pressure to give a residue. The residue was purified by silica gel chromatography, eluting with EtOAc in petroleum ether (10% to 35%) to afford the title product (500 mg, 76% yield, 0.886 mmol) as yellow oil. ESI-MS $[M+Na]^+$ Calc'd for $(C_{27}H_{37}BO_{12}Na^+)$ 587.23, found 587.2.

Following Scheme B, (2R,3R,4S,5S,6R)-2-(acetoxymethyl)-6-(2-methyl-4-(4,4,5,5-tetramethyl-1,3,2-dioxaborolan-2-yl)phenoxy)tetrahydro-2H-pyran-3,4,5-triyl triacetate (200 mg, 0.354 mmol) and 2-chloro-5-(trifluoromethyl)pyrazine (96 mg, 0.53 mmol) were reacted via the standard Suzuki coupling procedure (60 min at 80° C.), followed by deprotection protocol A (30 min at 25° C.), further purified by HPLC with conditions Column: XBridge Shield RP18 OBD column, Sum, 30*150 mm; Mobile Phase A: Water (10 mmol/L $NH_4HCO_3$+0.1% $NH_3·H_2O$), Mobile Phase B: ACN (acetonitrile); Flow rate: 60 mL/min; Gradient: 20% B to 40% B in 8 min; 254 nm; Rt: 7.75 min to afford the title product (35 mg, 0.084 mmol, 24% yield for two steps) as a white solid.

Formula: $C_{18}H_{19}F_3N_2O_6$. Exact Mass: 416.12, Molecular Weight: 416.35.

Analytical data: $^1$H NMR (300 MHz, Methanol-$d_4$) δ 9.24 (d, J=1.5 Hz, 1H), 9.00 (d, J=1.4 Hz, 1H), 8.11-7.95 (m, 2H), 7.42 (d, J=8.4 Hz, 1H), 5.66 (d, J=1.5 Hz, 1H), 4.11 (dd, J=3.4 Hz, 1.8 Hz, 1H), 3.99 (dd, J=9.4 Hz, 3.4 Hz, 1H), 3.84-3.70 (m, 3H), 3.57-3.54 (m, 1H), 2.36 (s, 3H). ESI-MS [M+H]$^+$ Calc'd for ($C_{18}H_{19}F_3N_2O_6H^+$) 417.12, found 417.15.

Example 2

(2R,3S,4S,5S,6R)-2-(2-Fluoro-6-(trifluoromethyl)-4-(5-(trifluoromethyl)pyrazin-2-yl)phenoxy)-6-(hydroxymethyl)tetrahydro-2H-pyran-3,4,5-triol

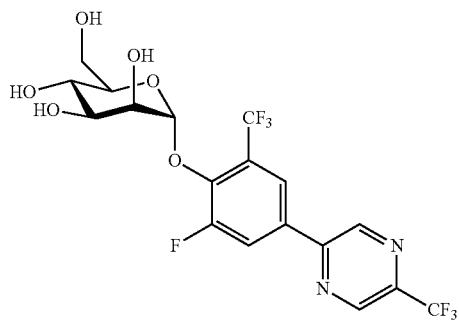

(2R,3R,4S,5S,6R)-2-(Acetoxymethyl)-6-(4-bromo-2-fluoro-6-(trifluoromethyl)phenoxy)tetrahydro-2H-pyran-3,4,5-triyl triacetate: To a solution of (2R,3S,4S,5R,6R)-6-(acetoxymethyl)tetrahydro-2H-pyran-2,3,4,5-tetrayl tetraacetate (3.762 g, 9.64 mmol) and 4-bromo-2-fluoro-6-(trifluoromethyl)phenol (3.0 g, 11.58 mmol) in DCM (20 mL) were added $BF_3$-$Et_2O$ (4.15 g, 29 mmol) at 25° C. The reaction mixture was stirred at 45° C. for 16 h. After completion, the reaction mixture was quenched with water (20 mL), extracted with DCM (3×20 mL). The organic layers were combined, washed with water (2×10 mL), dried over $Na_2SO_4$ filtered, and concentrated to get a residue. The residue was dissolved with EtOAc, pre-adsorbed by evaporation onto silica gel and loaded to a silica column, then purified by column chromatography, eluting with PE:EA=1:1 to afford the title product (400 mg, 0.68 mmol, 7% yield) as orange oil. ESI-MS [M+Na]$^+$ Calc'd for ($C_{21}H_{21}BrF_4O_{10}Na^+$) 611.03, found 611.03

(2R,3R,4S,5S,6R)-2-(Acetoxymethyl)-6-(2-fluoro-4-(4,4,5,5-tetramethyl-1,3,2-dioxaborolan-2-yl)-6-(trifluoromethyl)phenoxy)tetrahydro-2H-pyran-3,4,5-triyl triacetate To a solution of (2R,3R,4S,5S,6R)-2-(acetoxymethyl)-6-(4-bromo-2-fluoro-6-(trifluoromethyl)phenoxy)tetrahydro-2H-pyran-3,4,5-triyl triacetate (400 mg, 0.68 mmol) and 4,4,4',4',5,5,5',5'-octamethyl-2,2'-bi(1,3,2-dioxaborolane) (180 mg, 0.71 mmol) in dioxane (3 mL) were added Pd(dppf)$Cl_2$·$CH_2Cl_2$ (55 mg, 0.067 mmol) and KOAc (200 mg, 2.04 mmol) at 25° C. under $N_2$. Then, the reaction mixture was heated to 80° C. for 2 h under $N_2$. After completion, the reaction mixture was quenched with water (5 mL) and extracted with EtOAc (3×5 mL). The combined organic layers were washed with brine (5 mL), dried over $Na_2SO_4$ and filtered. The filtrate was concentrated under reduced pressure to give a residue. The residue was purified by silica gel chromatography, eluting with EtOAc in petroleum ether (10% to 40%) to afford the title product (280 mg, 0.44 mmol, 65% yield) as white oil. ESI-MS [M+NH$_4$]$^+$ Calc'd for ($C_{27}H_{33}BF_4O_{12}NH_4^+$) 654.23, found, 654.39.

(2R,3S,4S,5S,6R)-2-(2-Fluoro-6-(trifluoromethyl)-4-(5-(trifluoromethyl)pyrazin-2-yl)phenoxy)-6-(hydroxymethyl)tetrahydro-2H-pyran-3,4,5-triol Following Scheme B, (2R,3R,4S,5S,6R)-2-(acetoxymethyl)-6-(2-fluoro-4-(4,4,5,5-tetramethyl-1,3,2-dioxaborolan-2-yl)-6-(trifluoromethyl)phenoxy)tetrahydro-2H-pyran-3,4,5-triyl triacetate_(300 mg, 0.47 mmol) and 2-chloro-5-(trifluoromethyl)pyrazine (90 mg, 0.49 mmol) were reacted via the standard Suzuki coupling procedure (60 min at 80° C.), followed by deprotection protocol A (60 min at 25° C.), further purified by HPLC with conditions: Column: XBridge Shield RP C18 OBD 5 um, 19*150 mm; Mobile Phase A: Water (10 mM $NH_4HCO_3$), Mobile Phase B: ACN; Flow rate: 25 mL/min; Gradient: 31% B to 38% B in 11 min; 220 nm; Rt: 9.10 min to afford the desired product (30 mg, 0.061 mmol, 13% yield for two steps) as a white solid.

Formula: $C_{18}H_{15}F_7N_2O_6$. Exact Mass: 488.08, Molecular Weight: 488.31

Analytical data: $^1$H NMR (300 MHz, Methanol-$d_4$) δ 9.39 (d, J=1.4 Hz, 1H), 9.17-9.06 (m, 1H), 8.47-8.31 (m, 2H), 5.79 (s, 1H), 4.21 (dd, J=3.3 Hz, 1.8 Hz, 1H), 3.96 (dd, J=8.9 Hz, 3.3 Hz, 1H), 3.90-3.75 (m, 4H). ESI-MS [M+Na]$^+$ Calc'd for ($C_{18}H_{15}F_7N_2O_6Na^+$) 511.07, found 511.05.

Example 3

(2R,3S,4S,5S,6R)-2-(Hydroxymethyl)-6-(2-(trifluoromethyl)-4-(5-(trifluoromethyl)pyrazin-2-yl)phenoxy)tetrahydro-2H-pyran-3,4,5-triol

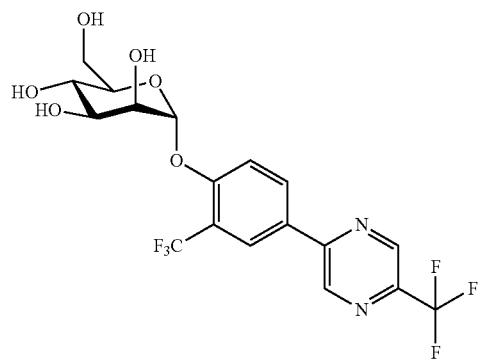

(2R,3R,4S,5S,6R)-2-(Acetoxymethyl)-6-(4-bromo-2-(trifluoromethyl)phenoxy)tetrahydro-2H-pyran-3,4,5-triyl triacetate: To a solution of (2R,3S,4S,5R,6R)-6-(acetoxymethyl)tetrahydro-2H-pyran-2,3,4,5-tetrayl tetraacetate (8.0 g, 21 mmol) and 4-bromo-2-(trifluoromethyl)phenol (5.0 g, 21 mmol) in DCM (20 mL) was added BF$_3$-Et$_2$O (8.1 mL) at 25° C. The reaction mixture was stirred at 45° C. for 18 h. After completion, the reaction mixture was concentrated to get a residue. The residue was purified by column chromatography, eluting with (PE:EA=3:1) to afford the title product (2.6 g, 4.55 mmol, 22% yield) as yellow oil. ESI-MS [M+Na]$^+$ Calc'd for (C$_{21}$H$_{22}$BrF$_3$O$_{10}$Na$^+$) 593.02, found 593.0.

(2R,3R,4S,5S,6R)-2-(Acetoxymethyl)-6-(4-(4,4,5,5-tetramethyl-1,3,2-dioxaborolan-2-yl)-2-(trifluoromethyl)phenoxy)tetrahydro-2H-pyran-3,4,5-triyl triacetate To a solution of (2R,3R,4S,5S,6R)-2-(Acetoxymethyl)-6-(4-bromo-2-(trifluoromethyl)phenoxy)tetrahydro-2H-pyran-3,4,5-triyl triacetate (500 mg 0.88 mmol) in dioxane (5 ml) was added 4,4,4',4',5,5,5',5'-octamethyl-2,2'-bi(1,3,2-dioxaborolane) (267 mg 1.1 mmol), Pd(dppf)Cl$_2$ (64 mg 0.09 mmol) and KOAc (257 mg 2.6 mmol) at 25° C. The resulting solution was stirred for 3 h at 80° C. under N$_2$. After completion, the reaction mixture was quenched with water (5 mL) and extracted with EtOAc (3×5 mL). The organic layers were combined and washed with brine (5 mL), dried over Na$_2$SO$_4$ and filtered. The filtrate was concentrated under reduced pressure to give a residue. The residue was purified by silica gel chromatography, eluting with EtOAc in petroleum ether (0% to 40%) to afford the title product (460 mg, 0.74 mmol, 85% yield) as yellow oil. ESI-MS [M+Na]$^+$ Calc'd for (C$_{27}$H$_{34}$BF$_3$O$_{12}$Na$^+$) 641.21, found, 641.15.

(2R,3S,4S,5S,6R)-2-(Hydroxymethyl)-6-(2-(trifluoromethyl)-4-(5-(trifluoromethyl)pyrazin-2-yl)phenoxy)tetrahydro-2H-pyran-3,4,5-triol Following Scheme B, (2R,3R,4S,5S,6R)-2-(acetoxymethyl)-6-(4-(4,4,5,5-tetramethyl-1,3,2-dioxaborolan-2-yl)-2-(trifluoromethyl)phenoxy)tetrahydro-2H-pyran-3,4,5-triyl triacetate (460 mg, 0.74 mmol and 2-chloro-5-(trifluoromethyl)pyrazine (136 mg 0.74 mmol) were reacted via the standard Suzuki coupling procedure (4 h at 80° C.), followed by deprotection protocol A (30 min at 25° C.), further purified by HPLC with conditions: XBridge Shield RP18 OBD Column 30*150 mm, 5 um; Mobile Phase A:Water (10 mM NH$_4$HCO$_3$), Mobile Phase B: ACN; Flow rate: 60 mL/min; Gradient: 27% B to 45% B in 10 min; 254 nm; Rt: 9.03 min to afford the desired product (22 mg, 0.047 mmol, 6% yield for two steps) as a white solid.

Formula: C$_{18}$H$_{16}$F$_6$N$_2$O$_6$ Exact Mass: 470.09 Molecular Weight: 470.32

Analytical data: $^1$H NMR (300 MHz, Methanol-d$_4$) δ 9.34 (s, 1H), 9.08 (s, 1H), 8.53 (d, J=2.2 Hz, 1H), 8.47 (d, J=8.9 Hz, 1H), 7.71 (d, J=8.8 Hz, 1H), 5.76 (d, J=1.8 Hz, 1H), 4.09 (dd, J=3.4 Hz, 1.9 Hz, 1H), 3.96 (dd, J=9.5 Hz, 3.4 Hz, 1H), 3.87-3.67 (m, 3H), 3.59-3.55 (m, 1H). ESI-MS [M+H]$^+$ Calc'd for (C$_{18}$H$_{16}$F$_6$N$_2$O$_6$H$^+$) 471.09, found 471.15.

Example 4

5-Fluoro-3'-methyl-4'-(((2R,3S,4S,5S,6R)-3,4,5-trihydroxy-6-(hydroxymethyl)tetrahydro-2H-pyran-2-yl)oxy)-[1,1'-biphenyl]-3-carbonitrile

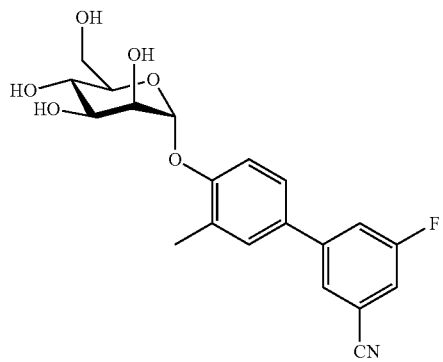

(2R,3R,4S,5S,6R)-2-(acetoxymethyl)-6-((3'-cyano-5'-fluoro-3-methyl-[1,1'-biphenyl]-4-yl)oxy)tetrahydro-2H-pyran-3,4,5-triyl triacetate To a solution of (2R,3R,4S,5S,6R)-2-(Acetoxymethyl)-6-(4-bromo-2-methylphenoxy)tetrahydro-2H-pyran-3,4,5-triyl triacetate (500 mg, 0.97 mmol1), 3-fluoro, 5-cyano phenyl boronic acid (170 mg, 1.03 mmol), Tetrakis palladium triphenylphosphine (60 mg. 0.05 mmol) and cesium carbonate (1 g, 3.0 mmol) in dioxane:H$_2$O (4:1, 15 mL) were combined at 25° C. The reaction was warmed to 80° C. and stirred for 1 h, a LCMS analysis of the reaction mixture indicated that the reaction was complete. The reaction mixture was cooled to 25° C. and quenched with water (10 mL). The reaction was then extracted with EA (30 mL×3). The combined organic phases were dried over sodium sulfate, filtered and concentrated under reduced pressure to afford a residue which was purified by silica gel chromatography (EA/PE 0-50%). The fractions containing the product were combined and concentrated to afford (2R,3R,4S,5S,6R)-2-(acetoxymethyl)-6-((3'-cyano-5'-fluoro-3-methyl-[1,1'-biphenyl]-4-yl)oxy)tetrahydro-2H-pyran-3,4,5-triyl triacetate (330 mg, 0.59 mmol, 61% yield).

5-Fluoro-3'-methyl-4'-(((2R,3S,4S,5S,6R)-3,4,5-trihydroxy-6-(hydroxymethyl)tetrahydro-2H-pyran-2-yl)oxy)-[1,1'-biphenyl]-3-carbonitrile To a solution (2R,3R,4S,5S,6R)-2-(acetoxymethyl)-6-((3'-cyano-5'-fluoro-3-methyl-[1,1'-biphenyl]-4-yl)oxy)tetrahydro-2H-pyran-3,4,5-triyl triacetate (330 mg, 0.59 mmol) in MeOH (5 mL) at 0° C. was added NaOMe (1 mL, 0.5N in MeOH) dropwise until a pH of 9 was achieved. A LCMS analysis indicated the reaction was complete. The solvent was removed under reduced pressure and the residue was dissolved in MeOH (5 mL) and purified by prep HPLC with conditions: XBridge Shield RP18 OBD Column 30*150 mm, 5 um; Mobile Phase A:Water(10 mmol/L NH$_4$HCO$_3$), Mobile Phase B: ACN; Flow rate: 60 mL/min; Gradient: 23-43% B in 8 min; 254 nm; Rt: 7.27 min to afford the desired (118 mgs, 0.30 mmol, 51%) as a white solid.

Formula: C$_{20}$H$_{20}$FNO$_6$ Exact Mass: 389.13 Molecular Weight: 389.38

Analytical data: H¹NMR (300 MHz, MeOD) δ 7.80 (t, J=1.6 Hz, 1H), 7.69-7.66 (m, 1H), 7.49-7.44 (m, 3H), 7.33 (d, J=8.4 Hz, 1H), 5.57 (d, J=1.6 Hz, 1H), 4.07-4.06 (m, 1H), 3.96 (dd, J=3.2, 9.2 Hz, 1H), 3.79-3.70 (m, 3H), 3.58-3.54 (m, 1H), 2.36 (s, 3H). ESI-MS [M+H]$^+$ Calc'd for ($C_{20}H_{20}FNO_6H^+$), 390.14, found, 390.127.

Example 5

(2R,3S,4S,5S,6R)-2-(hydroxymethyl)-6-(2-methyl-4-(4-(trifluoromethyl)pyridin-2-yl)phenoxy)tetrahydro-2H-pyran-3,4,5-triol

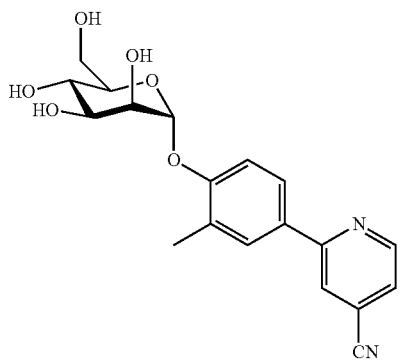

(2R,3R,4S,5S,6R)-2-(Acetoxymethyl)-6-(2-methyl-4-(4-(trifluoromethyl)pyridin-2-yl)phenoxy)tetrahydro-2H-pyran-3,4,5-triyl triacetate (2R,3R,4S,5S,6R)-2-(Acetoxymethyl)-6-(2-methyl-4-(4,4,5,5-tetramethyl-1,3,2-dioxaborolan-2-yl)phenoxy)tetrahydro-2H-pyran-3,4,5-triyl triacetate (500 mg, 0.89 mmol) was dissolved in dioxane (8 mL) and H$_2$O (2 mL). 2-Chloro, 4-trifluoromethyl pyridine (160 mg, 0.47 mmol), Pd(PPh$_3$)$_4$ (52 mg, 0.045 mmol) and Cesium carbonate (870 mg, 2.7 mmol) were added to the reaction mixture. The reaction mixture was flushed with nitrogen and heated to 80° C. for 4 h, where a LCMS analysis indicated it was complete. The reaction mixture was cooled to 25° C. and diluted with H$_2$O (10 mL). The reaction mixture was then extracted with ethyl acetate (10 mL×3), the organic phase was separated, combined and washed with H$_2$O (5 mL×3), then it was separated and dried over Na$_2$SO$_4$ and filtered. The filtrate was concentrated to get a residue of (2R,3R,4S,5S,6R)-2-(acetoxymethyl)-6-(2-methyl-4-(4-(trifluoromethyl)pyridin-2-yl)phenoxy)tetrahydro-2H-pyran-3,4,5-triyl triacetate (300 mg, 0.514 mmol, 57%, crude) which was used in the next step without further purification.

(2R,3S,4S,5S,6R)-2-(hydroxymethyl)-6-(2-methyl-4-(4-(trifluoromethyl)pyridin-2-yl)phenoxy)tetrahydro-2H-pyran-3,4,5-triol (2R,3R,4S,5S,6R)-2-(acetoxymethyl)-6-(2-methyl-4-(4-(trifluoromethyl)pyridin-2-yl)phenoxy)tetrahydro-2H-pyran-3,4,5-triyl triacetate (280 mg, 0.48 mmol) was dissolved in MeOH (5 mL) and NaOMe in MeOH (0.5 N) was added dropwise until a pH of 9 was achieved. The reaction was complete. The reaction mixture was diluted with MeOH (5 mL) and purified by further purified by HPLC with conditions: XBridge Shield RP18 OBD Column 30*150 mm, 5 um; Mobile Phase A:Water(10 mM NH$_4$HCO$_3$), Mobile Phase B: ACN; Flow rate: 60 mL/min; Gradient: 20-50% B in 10 min; 254 nm; Rt: 8.68 min to afford (2R,3S,4S,5S,6R)-2-(hydroxymethyl)-6-(2-methyl-4-(4-(trifluoromethyl)pyridin-2-yl)phenoxy)tetrahydro-2H-pyran-3,4,5-triol (87 mg, 0.20 mmol, 57%) as a white solid.

Formula: $C_{19}H_{20}F_3NO_6$ Exact Mass: 415.12 Molecular Weight: 415.37

Analytical data: H¹NMR (300 MHz, MeOD) δ 8.82 (d, J=5.1 Hz, 1H), 8.06 (s, 1H), 7.95-7.84 (m, 2H), 7.60-7.52 (m, 1H), 7.38 (d, J=8.5 Hz, 1H), 5.63 (d, J=1.94 Hz, 1H), 4.10 (d, J=3.4 Hz, 1H), 3.99 (dd, J=4.03, 1.7 Hz, 1H), 3.86-3.69 (m, 3H), 3.59-3.54 (m, 1H), 2.35 (s, 3H). ESI-MS [M+H]$^+$ Calc'd for ($C_{19}H_{20}F_3NOH^+$) 416.13, found 416.124.

Other Example compounds in Table 1 were made using analogous methods.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound of formula I, or a pharmaceutically acceptable salt thereof,

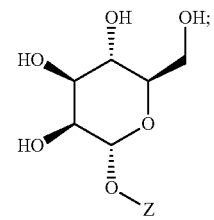

in which

Z is

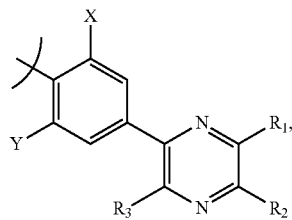

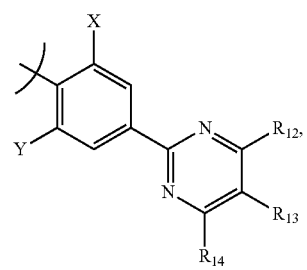

-continued

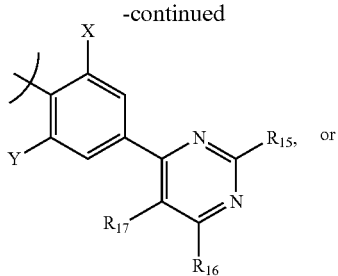

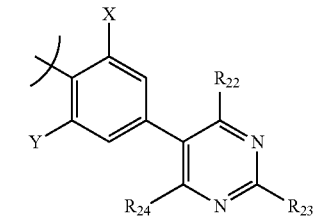

wherein:
X is CH₃, Cl, or CF₃;
Y is H or F; and
each R₁, R₂, R₃, R₁₂, R₁₃, R₁₄, R₁₅, R₁₆, R₁₇, R₂₂, R₂₃, and R₂₄ are independently selected from the group consisting of hydrogen, CN, F, $C_{3-6}$cycloalkyl, $C_{1-6}$alkyl, $-N(C_{1-6}alkyl)_2$, $-OC_{1-6}$alkyl, CF₃, and

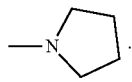

2. A compound or pharmaceutically acceptable salt according to claim 1, wherein Z is:

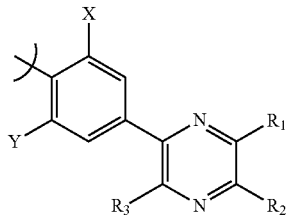

wherein one of R₁, R₂ and R₃ are selected from the group consisting of CN, F, $C_{3-6}$cycloalkyl, $C_{1-6}$alkyl, $-N(C_{1-6}$ alkyl$)_2$, $-OC_{1-6}$alkyl, CF₃, and

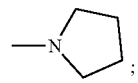

and the others are hydrogen.

3. A compound or pharmaceutically acceptable salt according to claim 2, wherein one of R₁, R₂ and R₃ are selected from the group consisting of cyclopropyl, —CH₃, CF₃, and

and the others are hydrogen.

4. A compound or pharmaceutically acceptable salt according to claim 3, wherein R₁ and R₃ are both hydrogen and R₂ is selected from the group consisting of cyclopropyl, —CH₃, CF₃, and

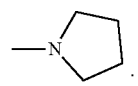

5. A compound or pharmaceutically acceptable salt thereof according to claim 1, wherein either:
X is CH₃ and Y is H; or
X is CF₃ and Y is F or H; or
X is Cl and Y is H.

6. A compound or pharmaceutically acceptable salt thereof according to claim 5, wherein X is CH₃ and Y is H.

7. A compound of claim 1 selected from the group consisting of:
(2R,3S,4S,5S,6R)-2-(Hydroxymethyl)-6-(2-methyl-4-(5-(trifluoromethyl) pyrazin-2-yl) phenoxy) tetrahydro-2H-pyran-3,4,5-triol,
(2R,3S,4S,5S,6R)-2-(2-Fluoro-6-(trifluoromethyl)-4-(5-(trifluoromethyl) pyrazin-2-yl) phenoxy)-6-(hydroxymethyl) tetrahydro-2H-pyran-3,4,5-triol, and
(2R,3S,4S,5S,6R)-2-(Hydroxymethyl)-6-(2-(trifluoromethyl)-4-(5-(trifluoromethyl) pyrazin-2-yl) phenoxy) tetrahydro-2H-pyran-3,4,5-triol,
or a pharmaceutically acceptable salt thereof.

* * * * *